(12) United States Patent
Li et al.

(10) Patent No.: US 9,194,851 B2
(45) Date of Patent: Nov. 24, 2015

(54) METHODS AND MATERIALS FOR THE DETECTION OF MELAMINE

(71) Applicant: The Regents of the University of California, Oakland, CA (US)

(72) Inventors: Na Li, Palmetto Bay, FL (US); Fang Wei, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/296,034

(22) Filed: Jun. 4, 2014

(65) Prior Publication Data
US 2015/0004713 A1 Jan. 1, 2015

Related U.S. Application Data

(63) Continuation of application No. 13/148,025, filed as application No. PCT/US2010/000323 on Feb. 5, 2010, now abandoned.

(60) Provisional application No. 61/150,177, filed on Feb. 5, 2009.

(51) Int. Cl.
*G01N 31/22* (2006.01)
*G01N 21/552* (2014.01)
*G01N 21/78* (2006.01)
*G01N 21/82* (2006.01)
*G01N 21/00* (2006.01)
*B82Y 15/00* (2011.01)

(52) U.S. Cl.
CPC .............. *G01N 31/22* (2013.01); *G01N 21/554* (2013.01); *G01N 21/78* (2013.01); *G01N 21/82* (2013.01); *B82Y 15/00* (2013.01); *Y10S 977/773* (2013.01); *Y10S 977/81* (2013.01); *Y10S 977/921* (2013.01); *Y10T 436/147777* (2015.01)

(58) Field of Classification Search
CPC ... G01N 21/658; G01N 21/554; G01N 31/22; G01N 21/82; G01N 21/78; Y10T 426/147777; Y10S 977/773; Y10S 977/81; Y10S 977/921; B82Y 15/00
USPC ............... 436/23, 106, 98; 977/773, 810, 902
See application file for complete search history.

(56) References Cited

U.S. PATENT DOCUMENTS 6,432,717 B1 * 8/2002 Fernando ...................... 436/106
2011/0207231 A1 * 8/2011 Natan et al. ..................... 436/98

* cited by examiner

*Primary Examiner* — Rebecca M Fritchman
(74) *Attorney, Agent, or Firm* — Foley & Lardner LLP; Cliff Z. Liu

(57) ABSTRACT

Methods and materials for the detection of melamine in test samples such as foodstuffs are described. Embodiments of the invention comprise combining a test sample suspected of containing melamine with a particle that produces a colorimetric and/or turbidimetric signal that is dependent upon the concentration of melamine in the test sample. In certain embodiments of the invention, the particles and test sample are combined together with a chemical compound selected to induce the aggregation melamine in a manner that amplifies the colorimetric and/or turbidimetric signal of the assay. In some embodiments of the invention, the aggregation inducing agent is not physically coupled to the particles used in the assays. In other embodiments of the invention, the aggregation inducing agent is physically coupled to the particles used in these assays.

5 Claims, 24 Drawing Sheets

MELAMINE CONCENTRATION

MELAMINE CONCENTRATION 1     2     3     4     5 pH 7
pH 6-7
pH 5-6
pH 3-4
pH <0

METHODS AND MATERIALS FOR THE DETECTION OF MELAMINE

CROSS REFERENCE TO RELATED APPLICATIONS

This application is a continuation of U.S. application Ser. No. 13/148,025, filed Aug. 4, 2011, which is a National Stage Entry of PCT/US2010/000323, filed Feb. 5, 2010, which claims the benefit under Section 119(e) from U.S. provisional Application Ser. No. 61/150,177, filed Feb. 5, 2009, the contents of which are incorporated herein by reference:

STATEMENT OF GOVERNMENT SUPPORT

This invention was made with government support under 0730689 awarded by the National Science Foundation. The government has certain rights in the invention.

BACKGROUND OF THE INVENTION

1. Field of the Invention

This invention relates to methods and materials useful for the detection of melamine.

2. Background.

Melamine (1,3,5-triazine-2,4,6-triamine) is an organic compound used extensively as a raw material in the preparation of polymers for the manufacture of a wide range of products, including fabrics, laminates, adhesives, molding compounds, coatings, and flame retardants. Melamine is also used in some fertilizers and can be found as a metabolite of the pesticide, cyromazine. Despite the widespread use of melamine, consumer exposure to melamine is considered to be low.

Melamine by itself is nontoxic in low doses, but when combined with cyanuric acid it can cause fatal kidney stones due to the formation of an insoluble melamine cyanurate. When melamine and cyanuric acid are absorbed into the bloodstream, they concentrate and interact in the urine-filled renal microtubules, crystallizing and forming large numbers of round, yellow crystals, which in turn block and damage the renal cells that line the tubes, causing the kidneys to malfunction. In low doses melamine is rapidly eliminated in the urine with a half-life in plasma of around three hours. In view of its pharmacokinetic profile, the US FDA has established that the tolerable daily intake (TDI) of melamine for adults is 0.63 mg/kg of body weight.

Melamine contamination in food may be due to migration from industrial uses, metabolic processing of pesticides, i.e. cyromazine, or intentional doping to modify nitrogen content analysis; for example in milk, where it is added to compensate for dilution with water (see, e.g. Szmant, H. H. in Organic Building Blocks of the Chemical Industry 1989, John Wiley and Sons; Hauck et al., Agric. Food Chem. 1964, 12, 147-151; U.S. Pat. No. 2,819,968; Newton et al., R. J. Animal Sci. 1978, 47, 1338-1344; Lim et al., J. Agric. Food Chem. 1990, 38, 860-864). High levels of melamine exposure have been associated with kidney failure and the adulteration of food products with melamine has resulted in the deaths of thousands of people and pets (see, e.g. Puschner et al., J. Vet. Diagn. Inv. 2007, 19, 616-624; Dobson et al., Toxicol. Sci. 2008, 106, 251-262; Hau et al., J. Am. Soc. Nephrol. 2009, 20, 245-250).

In view of its use, for example, as an adulterant of foodstuffs, a number of methods for detecting melamine in test samples have been developed. In conventional methods, a test substance to be analyzed for the presence of melamine is first purified using centrifugation and filtration techniques. Following these purification steps, liquid phase chromatography (LC) or high-pressure liquid chromatography (HPLC) is then performed prior to the final detection of melamine using a mass spectrum/spectrometer. Although these methods and other spectrum-based methods provide accurate techniques in determining melamine content, such methods are very labor intensive, time consuming, and expensive to perform. While enzyme-linked immunosorbent assays (ELISA) are also used to detect melamine, such techniques are similarly labor intensive, time consuming, and expensive to perform.

In view of the above, there is a need for inexpensive, accurate, simple, and fast methods for detecting the presence of melamine in test samples.

SUMMARY OF THE INVENTION

As discussed in detail below, the instant disclosure provides a number of unique methods for the simple, rapid and specific detection of melamine. The methods and materials disclosed herein allow artisans to overcome a number of problems associated with conventional melamine assays.

The invention disclosed herein has a number of embodiments. A typical embodiment of the invention is a method of observing the presence or absence of melamine in a test sample by combining the test sample with a plurality of particles in an aqueous media, wherein the particles have an average diameter of between 1 and 2500 nm; mixing the test sample with the particles so as to allow melamine, if present in the test sample, to interact with the particles; monitoring the media to observe a change in color or turbidity; and then correlating changes in the color or turbidity of the media with the presence or absence of melamine in the test sample. In this way, the presence or absence of melamine in a test sample can be easily and rapidly observed.

Certain methodological embodiments of the invention include further steps that can facilitate the detection of melamine in test samples such as combining the test sample with a melamine aggregation inducing agent (e.g. cyanuric acid or another aggregation inducing agent disclosed herein). In some embodiments of the invention, the aggregation inducing agent is coupled to the particles. In other embodiments of the invention, the aggregation inducing agent is not coupled to the particles. In other embodiments of the invention, the method is performed without the addition of a melamine aggregation inducing agent.

In typical methodological embodiments of the invention, the media is monitored with the naked eye. In certain embodiments, the media is monitored to observe changes in color. Optionally, changes in media color are observed with a spectrometer. In other methodological embodiments, the media is monitored to observe changes in turbidity. Optionally, changes in media turbidity are observed with a turbidimeter. In certain embodiments of the invention, the media is monitored to observe changes in both color and turbidity. In some embodiments of the invention, correlating changes in color or turbidity with the presence or absence of melamine in the test sample includes the step of comparing changes in color or turbidity in the test sample with changes in color or turbidity in a control sample having a known amount of melamine.

Another embodiment of the invention is a kit for the detection of melamine in a test sample comprising: particles having an average diameter of between 1 and 2500 nm; a melamine aggregation inducing agent; and instructions for using the kit to detect melamine in a test sample. Optionally in this kit, the particles are gold nanoparticles having an average diameter of between 1 and 25 nanometers. In certain embodiments of the invention the aggregation inducing agent is coupled to the particles and further comprises cyanuric acid or another aggregation inducing agent disclosed herein. In typical embodiments of the invention, the kit further includes a melamine control sample comprising a known amount of melamine.

Yet another embodiment of the invention is a composition of matter made by combining in an aqueous media: melamine; and particles having an average diameter of between 1 and 2500 nm; wherein the composition exhibits a color or a turbidity that is dependent upon the concentration of melamine in the composition. In certain embodiments, the particles in the composition are gold nanoparticles having an average diameter of between 1 and 25 nanometers. Optionally the composition further comprises an aggregation inducing agent selected from the group consisting of uric acid, cyanuric acid, uracil, acetic acid, oxalic acid, tannin, thymine, guanine, riboflavin, barbituric acid, maleimide, succinimide, diacetamide or glutarimide. In some embodiments of the invention, the aggregation inducing agent in the composition is coupled to the particles. In other embodiments of the invention, the composition further includes a polypeptide compound, for example casein or gluten.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figure 1:
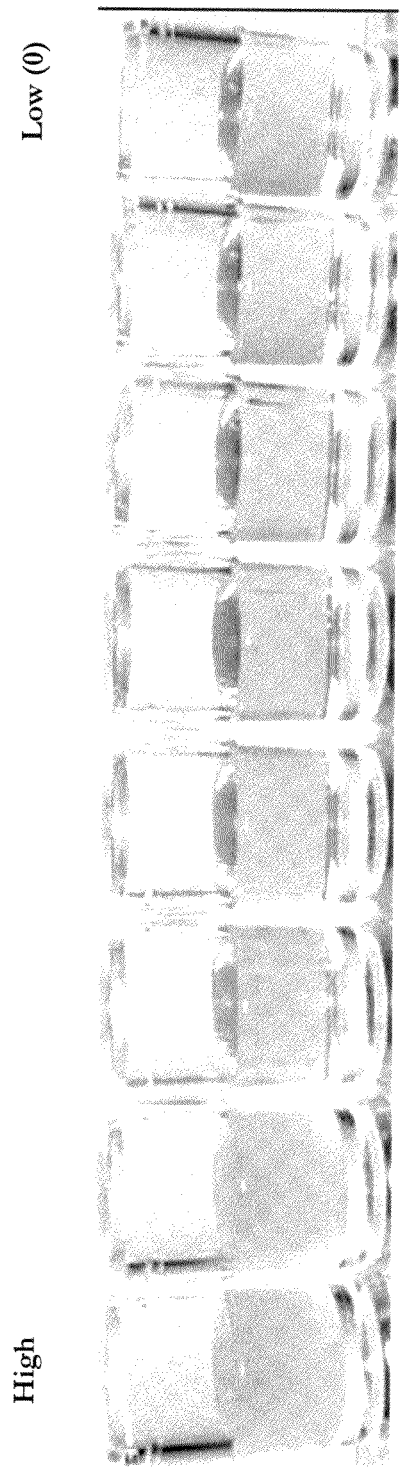
FIG. 1 provides a photograph showing the detection of melamine in water. Each well contains 80 ul gold nanoparticles (NP), 40 ul precipitation-inducing compound (cyanuric acid) and 80 ul DI water containing varying concentrations of melamine (decreasing from left to right). In these assays, the precipitation-inducing compound was not coupled to the nanoparticles.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

All publications mentioned herein are incorporated herein by reference to disclose and describe the methods and/or materials in connection with which the publications are cited. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "a particle" includes a plurality of particles and equivalents thereof known to those skilled in the art, and so forth. All numbers recited in the specification and associated claims that refer to values that can be numerically characterized with a value other than a whole number (e.g. between 1 and 2500 nm) are understood to be modified by the term "about".

Illustrative embodiments of the invention are described as follows. It will be apparent to one skilled in the art that various modifications and variations can be made in the present invention without departing from the scope of the appended claims. For example, features illustrated or described as part of one embodiment can be used on another embodiment to yield a still further embodiment.

1. Methods and Materials for the Colorimetric and/or Turbidimetric Detection of Melamine As noted above, conventional tests for the presence of melamine in foodstuffs such as milk products and other test samples are complicated, expensive and time consuming. The disclosure herein provides a number of unique methods for the simple, rapid and specific detection of melamine. The methods and materials disclosed herein allow artisans to overcome a number of problems associated with conventional melamine assays.

Embodiments of the invention comprise methods for the detection of melamine by combining a test sample suspected of containing melamine with a particle that produces a colorimetric and/or turbidimetric signal that is dependent upon the concentration of melamine in the test sample. In some embodiments of the invention, the particles and test sample are combined together with a chemical compound selected to induce the aggregation and/or precipitation of melamine in a manner that amplifies the colorimetric and/or turbidimetric signal of the assay. In other embodiments of the invention, the method is performed without the addition of a melamine aggregation inducing agent. In certain embodiments of the invention that use an aggregation inducing compound, the aggregation inducing compound is not physically coupled to the particles used in the assays. In other embodiments of the invention that use an aggregation inducing compound, the aggregation inducing compound is physically coupled to the particles used in the assays.

The invention disclosed herein has a number of embodiments. A typical embodiment of the invention is a method of observing the presence or absence of melamine in a test sample, the method comprising: combining the test sample with a plurality of particles in an aqueous media, wherein the particles have an average diameter of between 1 and 2500 nm; mixing the test sample with the particles so as to allow melamine, if present in the test sample, to interact with the particles; monitoring the media to observe a change in color or turbidity; and then correlating changes in the color or turbidity of the media with the presence or absence of melamine in the test sample, so that the presence or absence of melamine in a test sample is observed. In embodiments of the invention, test samples can be obtained from a wide variety of sources. Typically, the test sample is obtained from a source in which melamine is known to be used as an adulterant, for example foods such as pet food, milk and milk products such as infant formula, coffee, tea, biscuits, wafers, cookies and the like. In certain embodiments of the invention, the test sample is not pretreated prior to its combination with the particles. In other embodiments of the invention, the test sample is pretreated prior to its combination with the particles, for example a pretreatment comprising altering its pH, extraction, centrifugation, precipitation, filtration, dilution or the like.

Embodiments of the invention combine particles (e.g. ~10 nm gold nanoparticles) with melamine to produce a colorimetric and/or turbidimetric signal. In this context, the term "particle(s)" is used generically to denote a carrier structure which behaves as unit, and which is chemically and/or physically stable in the environments in which the particle is used (e.g. aqueous environments such as milk). Particles useful in embodiments of the invention can range in average diameter from 1 nm to 2500 nm in diameter. In certain embodiments of the invention, the particles can have an average diameter, for example one less than or equal to 1, 5, 10, 15, 20, 25, 30, 50, 100, 500, 750, 1000, 1250, 1500, 1750, 2000, 2250 or 2500 nm. A variety of materials can be used to form particles useful in embodiments of the invention including, for example, metals such as Au, Ag, Fe, Pt, Pd, Co, Cu, Ga, Ni, Ti, W, Rh, Cr and alloys and mixtures thereof. In addition, in certain embodiments the particles can be mixed with and/or formed from other materials such as polymeric materials (e.g. neoprene, nylon, PVC, polystyrene, polyethylene, polypropylene, polyacrylonitrile, thermoplastic polyamide, PVB, silicone, and the like). The particles can be of a variety shapes such as spheres, ellipsoids, rods, fibers, discs, bullets, barrels and the like. Embodiments of such particles include, for example, $SiO_2$ nanoparticles, carbon nanotubes, as well as semiconducting quantum dots and the like.

In certain embodiments of the invention, the particles are selected exhibit a constellation of characteristics (e.g. plasmon absorption properties) that make them exhibit alterations in color in the presence of different concentrations of melamine. While certain embodiments of the invention can use an aggregation inducing agent to modulate this colorimetric signal, other embodiments of the invention do not use such an agent, and instead rely on the unexpected interaction between particles and melamine as disclosed herein. The color change observed with gold nanoparticles (AuNPs) in the presence of different concentrations of melamine provides evidence of a strong interaction between AuNPs and melamine and is consistent with observations that molecules having certain constellations of amine moieties can bind strongly to AuNPs (see, e.g. Kumar et al., Langmuir, 2003, 19, 6277-6282; and Leff et al., Langmuir, 1996, 12, 4723-4730). Without being bound by a specific theory or principle, it is believed that exocyclic amines in melamine play an important role in the melamine-AuNP interaction. As noted above, certain embodiments of the invention that use particles having this constellation of characteristics (i.e. that result in colorimetric interactions with melamine) do not require a melamine aggregation inducing agent such as cyanuric acid. Such embodiments of the invention are desirable in certain contexts, for example due to the avoidance of costs (e.g. processing and cleanup costs) and/or technical steps (e.g. coupling reactions) that are associated with the use extra chemical compounds such as cyanuric acid, 1,6-dibromohexane and the like. Consequently, embodiments of the invention include the use of particles selected to have a constellation of surface plasmon characteristics that result in their colorimetric interactions with melamine in the absence of an aggregation inducing agent.

As noted above, certain methodological embodiments of the invention include the step of combining the test sample with a melamine aggregation/precipitation inducing agent. As disclosed herein, an illustrative aggregation inducing agent is cyanuric acid (1,3,5-triazine-2,4,6-triol), a chemical compound having the formula $(CNOH)_3$ (CAS number 108-80-5). In additional to cyanuric acid, other compounds that can facilitate the aggregation of melamine and are useful with embodiments of the invention include acetic acid, oxalic acid, tannin, and chemicals possessing certain imide groups such as thymine, uracil, guanine, uric acid, riboflavin, barbituric acid, maleimide, succinimide, diacetamide, glutarimide and their derivatives. As shown in Examples 1 and 2, a typical melamine aggregation inducing agent is cyanuric acid. In this embodiment, melamine-cyanuric acid complexes form and lead to aggregation due to an extensive two-dimensional network of hydrogen bonds between melamine and cyanuric acid, one reminiscent to that seen in DNA base pairing. In view of this understanding of the network of hydrogen bonds between melamine and cyanuric acid, in some embodiments of the invention, the melamine aggregation inducing agent comprises a constellation of carbonyl moieties and hydrogen moieties akin to those found on cyanuric acid and observed to form the network of hydrogen bonds with melamine. The aggregation inducing agents noted above are selected to exhibit a spectrum of aggregation inducing properties (e.g. an ability to induce the aggregation of melamine under a given set of media conditions). In this context, embodiments of the invention use selected different aggregation inducing agents for use in the detection of melamine, wherein the selection is based on the aggregation inducing properties of the agent in combination with the properties of the media and/or test sample that is being evaluated.

In certain embodiments of the invention that use an aggregation inducing agent, the aggregation inducing compound is not physically coupled to the particles used in the assays (e.g. those disclosed in Example 1 below). Such embodiments of the invention are desirable in certain contexts, for example due to their ease of use as well as their avoidance of the costs (e.g. processing and cleanup costs) and/or technical steps (e.g. coupling reactions) that are associated with the use of coupling compounds such as 1,6-dibromohexane and the like. In other embodiments of the invention that use an aggregation inducing compound, the aggregation inducing compound is physically coupled to the particles used in the assays (e.g. those disclosed in Example 2 below). Such embodiments of the invention are desirable in certain contexts, for example due to their high sensitivity in certain contexts, their ability to allow a greater control over the stoichiometric ratios of constituents used in the melamine assays (e.g. the ratio of particles to aggregation agent), and their associated ease in use (e.g. do to the reduction of the number of steps required to perform the assay).

Certain embodiments of the invention use particles coupled to an aggregation inducing agent in assays that monitor changes in media turbidity that result from the presence of melamine in the media. In such embodiments, the particles associate in the presence of melamine due to the aggregation inducing agent which associates with both the particles and the melamine. This association then produces changes in media turbidity. A variety of particles having an average diameter of between 1 and 2500 nm can be used in such embodiments. In some embodiments of the invention, the particles are at the lower end of this size range, for example the nanoparticles that are shown to be useful in assays designed to observe both colorimetric and turbidimetric changes to a media. In some embodiments of the invention (e.g. those that observe turbidity only), the particles are at the upper end of this size range, for example larger particles which facilitate the observations of turbidimetric changes to a media by the naked eye.

In typical methodological embodiments of the invention, the media is monitored by the naked eye (see, e.g. the photographs in FIGS. 4 and 6). In certain embodiments, the media is monitored to observe changes in color. Optionally, changes in media color are observed with a spectrometer (see, e.g. FIGS. 5-7). In other methodological embodiments, the media is monitored to observe changes in turbidity. Optionally, changes in media turbidity are observed with a turbidimeter. In certain embodiments of the invention, the media is monitored to observe changes in both color and turbidity. In some embodiments of the invention, correlating changes in color or turbidity with the presence or absence of melamine in the test sample includes the step of comparing changes in color or turbidity in the test sample with changes in color or turbidity in a control sample having a known amount of melamine.

Methodological embodiments of the invention have a number of advantages over conventional assays for the detection of melamine. For example, a significant advantage is the time saved by the methods of the invention, for example time saved by not having to perform complicated purification procedures (e.g. HPLC and the like) and/or obtain mass spectrometry readings etc. In this context, in certain embodiments of the invention, the assay provides a change in color or turbidity that is observable in less than 30, 20, 15, 10, 5, 4, 3, 2 or 1 minutes after combining the test sample with the particles.

In the fall of 2008, the U.S. FDA issued interim safety and risk assessment of melamine and melamine-related compounds in food. FDA has concluded that levels of melamine alone or cyanuric acid alone, at or below 1 part per million (ppm) in infant formula do not raise public health concerns. In food products other than infant formula, the FDA concludes that levels of melamine and melamine-related compounds below 2.5 parts per million (ppm) do not raise concerns. In this context, embodiments of the invention allow artisans to readily detect the threshold toxicity concentrations of melamine (e.g. as identified by the FDA) in a short time period. For example, in certain embodiments of the invention, the assay is able to detect a concentration of melamine in the test sample that is less than 20, 10, 5, 4, 3, 2.5, 2.0 or 1 parts per million (PPM). In certain embodiments of the invention, the assay is able to detect a concentration of melamine in a test sample that is less than 900, 800, 700, 600 or 500 parts per billion (PPB).

In a related aspect, embodiments of the invention include kits comprising a first container, a label on said container, and a composition contained within said container. In such kits, the composition includes particles having an average diameter of between 1 and 2500 nm and a melamine aggregation inducing agent that are used together to detect melamine. Typical embodiments include a label on said container, or a package insert included in said container indicates that the composition can be used to detect melamine. Optionally the kit includes additional elements such as a second container comprising a melamine control sample comprising a known amount of melamine. One illustrative embodiment of the invention is a kit for the detection of melamine in a test sample comprising: metallic nanoparticles; a melamine aggregation inducing agent; and instructions for using the kit to detect melamine in a test sample. Optionally in this kit, the particles are gold nanoparticles having an average diameter of between 1 and 25 nanometers. In certain embodiments of the invention the aggregation inducing agent is coupled to the particles and further comprises cyanuric acid or another aggregation inducing agent disclosed herein.

Yet another embodiment of the invention is a composition of matter made by combining in an aqueous media: melamine; and particles having an average diameter of between 1 and 2500 nm; wherein the composition exhibits a color or a turbidity that is dependent upon the concentration of melamine in the composition. In certain embodiments, the particles in the composition are gold nanoparticles having an average diameter of between 1 and 25 nanometers. Optionally the composition further comprises an aggregation inducing agent selected from the group consisting of uric acid, cyanuric acid, uracil, acetic acid, oxalic acid, tannin, thymine, guanine, riboflavin, barbituric acid, maleimide, succinimide, diacetamide and glutarimide. In some embodiments of the invention, the aggregation inducing agent in the composition is coupled to the particles. In other embodiments of the invention, the composition further includes a polypeptide compound, for example casein or gluten (i.e. polypeptides found in commonly adulterated food products).

In view of what is known in the art, using the disclosure provided herein one can generate a variety of different compositions having various concentrations of constituents. For example, as illustrated in the Examples below, the dynamic range of melamine detection can be adjusted by varying the concentrations of particles and aggregation inducing agent as well as the concentrations of salts and/or buffers present in the aqueous media (see, e.g. Example 1). Therefore, the concentration boundaries for NP and agents such as cyanuric acid in the compositions of the invention (as well as salts and buffers) can be varied depending upon the desired dynamic range of detection. In some embodiments of the invention, the particles are present in the composition at a concentration of between 1 and 1000 nM. In some embodiments where the particles comprise gold nanoparticles, the particles are present in the composition at a concentration of between 0.00001% to 0.1% HAuCL4. Similarly, in some embodiments where the aggregation inducing agent comprises cyanuric acid or the like, the aggregation inducing agent is present in the composition at a concentration of between 10 ppm and 2000 ppm.

In embodiments of the invention, an aqueous media in which particles and a test sample are combined typically includes water and optionally, one or more salts such as sodium chloride, potassium chloride or the like and/or buffering agents such as acetate, phosphate or citrate buffers etc. In this context, the skilled artisan understands that a wide variety of salts and buffer systems are well known in the art that can be adapted for use with embodiments of the invention (e.g. buffer systems such as TRIS, HEPES, MOPS, PIPES, MES, MOPSO, TAPSO, POPSO, DIPSO, HEPPSO, CAPSO, AMPSO etc.).

2. Illustrative Embodiments of Colorimetric and/or Turbidimetric Methods for the Detection of Melamine As noted above, conventional assays for the detection of melamine require complicated purification processes and/or expensive materials and instruments. In embodiments of the invention disclosed herein, particles are used to produce colorimetric and/or turbidimetric changes in an aqueous media, changes that can be correlated with the presence and specific concentration of melamine.

Embodiments of the invention comprise methods for the detection of melamine by combining a test sample suspected of containing melamine with a particle that produces a colorimetric and/or turbidimetric signal that is dependent upon the concentration of melamine in the test sample. As shown for example in Example 1 below, in some embodiments of the invention, the particles and test sample are combined together with a chemical compound selected to induce the aggregation and/or precipitation of melamine in a manner that amplifies the colorimetric and/or turbidimetric signal of the assay. As also shown in Example 1 below, in other embodiments of the invention, the method is performed without the addition of a melamine aggregation inducing agent. In certain embodiments of the invention that use an aggregation inducing compound, the aggregation inducing compound is not physically coupled to the particles used in the assays, for example the embodiments disclosed in Example 1.

Aspects of method and material embodiments used in the colorimetric and/or turbidimetric detection of melamine are discussed below.

Colorimetric Assays Using Nanoparticles

Certain embodiments of the invention utilize nanoparticles (e.g. particles having at least one dimension of 100 nm or less). Nanoparticles (NPs) are of scientific interest as they have special properties according to their fine dimensions. Colorimetric change due to the aggregation is one of the interesting properties of nanoparticles. For some NPs, resonant scattering of light can produce hue of NP, especially when surface plasmon is involved. Those NPs including particles with different dimensions, materials (metal, organic, inorganic, quantum dots, polymer, mixture of several types of NPs, and biomolecules in nanometer scale). The color of those NPs is closely related to the interaction between NPs. Parameters including pH, ionic strength, surface charge and dimension of NPs have effects on the hue. For a specific type of NP, the color can also be adjusted by the parameters mentioned above. As disclosed herein, melamine is observed to exhibit a strong interaction with NPs, even in the absence of melamine aggregation inducing agents such as cyanuric acid. Specifically, mixing melamine with NPs causes dramatic color change of NPs, which indicates the existence of melamine.

The color change of AuNPs in the presence of melamine as disclosed for example in Example 1 below demonstrates the strong interaction between AuNPs and melamine. This discovery is consistent with observations that molecules having certain constellations of amine moieties can bind strongly to AuNPs (see, e.g. Kumar et al., Langmuir, 2003, 19, 6277-6282; and Leff et al., Langmuir, 1996, 12, 4723-4730).

Turbidimetric Assays

In certain embodiments of the invention, in order to modulate (typically to increase) the specificity of the assay, an aggregation inducing compound is introduced into the detection system to interact with melamine. Such compounds can, for example, facilitate assays that examine the turbidity of a processed test sample (e.g. using a turbidimeter). Regarding the interaction between such compounds and melamine that contribute to its aggregation, it can be electro-static interaction (anions), van der Waals interaction (aromatic compounds), hydrogen bond interaction (e.g. between —C=0, —OH, —NH2 moieties on a compound), and other such intermolecular interactions.

An aggregation inducing molecule can be used in embodiments of the invention in order to cause a specific aggregation and/or precipitation with melamine, and also amplify the color change in the NPs test. In certain embodiments of the invention, the NPs and small compounds have a coordination effects. NPs helps to form the aggregation/precipitation more easily and faster, while the aggregation/precipitation cause more obvious color change in NPs. Considering color change from interferents in the detecting sample, combination of NPs and aggregation/precipitation greatly improve the specificity. With dual signal readouts (e.g. color as well as turbidity), melamine can be specifically detected in a fast and simple way in a variety of contexts.

Combined Colorimetric and Turbidimetric Assays

Certain embodiments of the invention can observe dual signals of: (1) color; and (2) turbidity in melamine assays. Typically, the dual signal output is within seconds under ambient conditions. When melamine is mixed with both the nanoparticles and the precipitation-inducing chemical component, the specific colorimetric signals and turbidimetric precipitation signals can be generated simultaneously. Such dual observation assays are desirable in certain contexts, for example those where non-specific interferents other than melamine can produce either a either colorimetric change or a precipitation, but not dual signal outputs. In this context, low levels of melamine can be detected even in mixtures that are observed to contain interferents. This technology consequently allows a rapid detection of melamine with high specificity directly from mixtures, thus eliminating the need for expensive instrumentation and/or the time-consuming sample preparation process necessary for existing technologies.

Detection

In embodiments of the invention, color changes with different concentration of melamine can be easily observed by eye. In embodiments disclosed in Example 1, the sensitivity is from 0.5-200 ppm, depending on the substances for detection. Transparent samples typically have much higher limit of detection (LOD) than the complicated samples, such as milk and egg. The LOD satisfies most of the requirements for food safety determinations. Detailed spectroscopy studies also show a good correlation between concentration of melamine and the wavelength of the detecting sample. By using an absorption spectrometer in certain embodiments of the invention, the sensitivity can be increased, even with test samples comprising complicated mixtures of melamine in combination with other compounds.

As shown in the Examples below, in typical embodiments of the invention, the color change happens within seconds (e.g. between 1 and 100 s) after mixing test samples with NPs and the chemical compound. Typically in these assays, the amount of sample is on a µl level, usually between 1 and 500 µl. The NPs and chemical compounds may or may not be subjected to pre-treatment steps, such as temperature treatments (e.g. heating, freezing), purification, dilution and surface chemical modification and/or surface charge reconstitution. While the labeling of NPs is not required, it is desirable in certain applications of the disclosed methods.

As shown in Example 1 below, the color change of NPs with melamine can be controlled by modulating reaction conditions of the assay. Typically, the conditions modulated include: pH, ionic strength, concentration, temperature, electrical field, and magnetic field. These parameters can, for example, change the properties of the NP, thereby changing the interaction between NPs and melamine, which can then result in different colorimetric/turbidimetric signals being generated.

As shown by the data in Example 1, the detection process can be carried out simply by eye in most cases without the need for mechanical instrumentation. However, certain embodiments of the invention include use of instruments such as absorption spectrometers, light scattering meters, microscopes (optical, AFM, TEM, SEM), surface plasmon resonance devices, electrochemical workstations and the like.

In some embodiments of the invention, the assay can be designed as a simple test that requires minimal steps to obtain a readout (e.g. the single step of adding a test sample to a premixed assay media). Such embodiments are useful, for example, for assays carried out in the field and/or in undeveloped areas. In other embodiments of the invention, a high throughput assay for the detection of melamine can be performed (e.g. using a series of 96 well plates in an automated system etc.).

Figure 2:
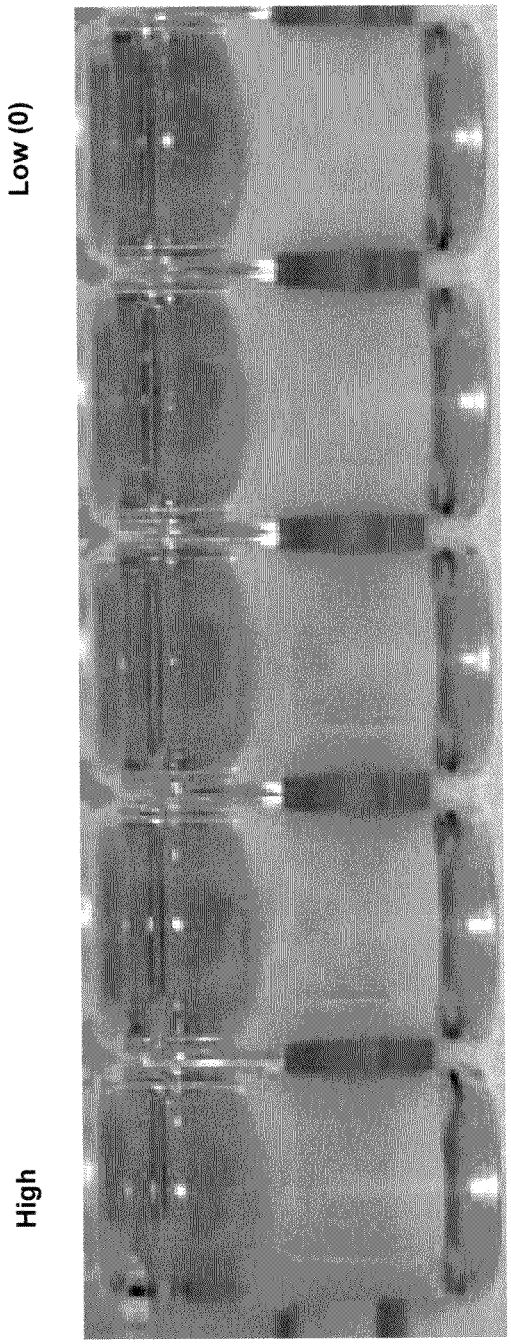
FIG. 2 provides a photograph showing the detection of melamine in whole milk. Each well contains 80 ul NP, 40 ul precipitation-inducing chemical and 80 ul whole milk samples containing varying concentrations of melamine (decreasing from left to right). For the whole milk samples, there is no other pre-treatment involved except diluting 2× times with water. In these assays, the precipitation-inducing chemical was not coupled to the nanoparticles.
Figure 3:
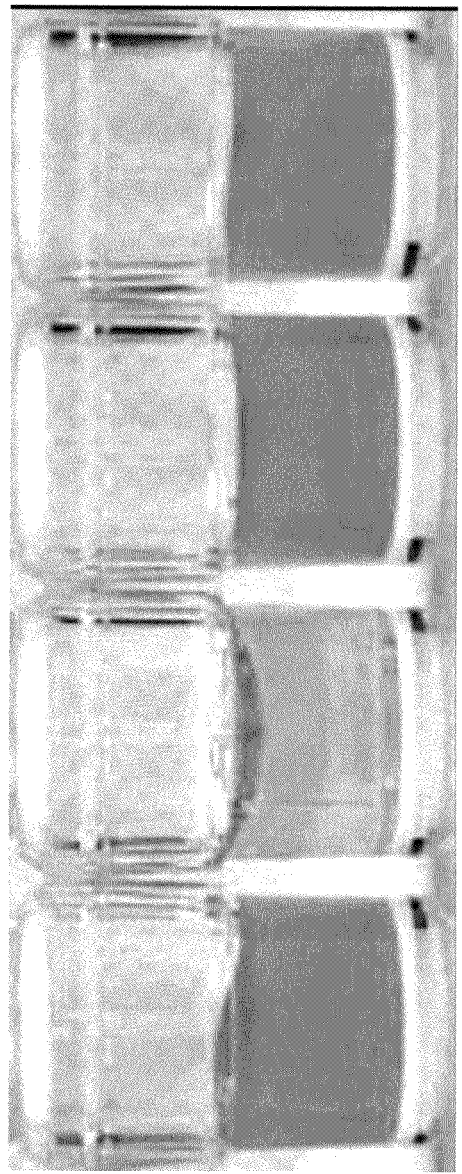
FIG. 3 provides a photograph showing the detection of melamine in egg. Each well contains 60 ul NP, 30 ul precipitation-inducing chemical compound and 60 ul egg white or egg yolk samples with or without melamine. For the egg samples, there is no other pre-treatment involved except diluting 8× times with water. In these assays, the precipitation-inducing chemical compound was not coupled to the nanoparticles.

The disclosure provided herein includes a number of illustrative assays for the detection of melamine in a variety of test samples under different assay conditions. The variety of assays disclosed herein demonstrates the versatility of embodiments of the invention. In the assays disclosed in FIGS. 1-3, the aggregation agent is not coupled to a particle. FIG. 1 provides a photograph showing the detection of melamine in water. FIG. 2 provides a photograph showing the detection of melamine in whole milk. FIG. 3 provides a photograph showing the detection of melamine in egg. Further illustrations of such embodiments of the invention are disclosed in Example 1 below.

3. Illustrative Embodiments of the Invention where a Melamine Aggregating Compound is Coupled to Particles As noted above, standard analytical methods like GC-MS and LC-MS protocols, as well as ELISA test kits are available for accurate melamine contamination detection (see, e.g. US FDA/CFSAN—Determination of Melamine and Cyanuric Acid residues in Infant Formula using LC-MS/MS—Lib. 4421). However, these techniques are not convenient for use in the home or locations such as food processing facilities.

Consequently simplified methods for the detection melamine contamination in a variety of food sources are highly desirable.

The dependence of the plasmon absorption properties characteristic of gold nanoparticles (NPs) on distance and aggregation states has led to useful colorimetric probes for detecting targets ranging from ions to cells (see, e.g. Rosi, et al., Chem. Rev. 2005, 105, 1547-1562; Wilson, R. Chem. Soc. Rev. 2008, 37, 2028-2045; Storhoff et al., J. Am. Chem. Soc. 1998, 120, 1959-1964; Storhoff et al., J. Am. Chem. Soc. 2000, 122, 4640-4650; Jain et al., J. Phys. Chem. B 2006, 110, 136-142; Liu et al., J. Am. Chem. Soc. 2003, 125, 6642-6643; Lee et al., Angew. Chem., Int. Ed. 2007, 46, 4093-4096; Daniel et al., A. J. Am. Chem. Soc. 2009, 131, 6362-6363; Jiang, et al., Angew Chem. Int. Ed. 2008, 47, 8601-8604; Elghanian et al., Science 1997, 277, 1078-1081; Nam et al., J. Am. Chem. Soc. 2002, 124, 3820-3821; and Medley et al., Anal. Chem. 2008, 80, 1067-1072). As disclosed herein, by taking advantage of specific H-bonding interactions between melamine and isocyanuric acid (see, e.g. Whitesides et al., Acc. Chem. Res. 1995, 28, 37-44; and Seto et al., J. Am. Chem. Soc. 1993, 115, 1330-1340), it is possible to develop surface functionalized NPs for the direct colorimetric visualization of melamine contamination. Furthermore, it is possible to apply these optical nanomaterials for the detection of melamine in milk by using a simple solvent extraction procedure.

As shown for example by the disclosure in Example 2 below, metallic nanoparticles coupled to a melamine aggregating agent can be exploited for melamine diagnosis in food, such as milk. This disclosure is consistent with what is observed in other detection systems known in the art, for example the detection of mercury, trinitrotoluene (TNT) using metallic nanoparticles (see, e.g. Lee et al., *Chem. Int. Ed.* 2007, 46, 4093-4096; Huang et al., *Angew. Chem. Int. Ed* 2007, 46, 6824-6828; Li et al., *Angew. Chem. Int. Ed* 2008, 47, 3927-3931; Ye et al., *Angew. Chem. Int. Ed* 2008, 47, 8386-8389; and Jiang et al., *Angew Chem. Int. Ed* 2008, 47, 8601-8604).

An illustrative embodiment of the invention is a method of observing the presence or absence of melamine in a test sample by combining the test sample with a plurality of particles in an aqueous media, wherein the particles have an average diameter of between 1 and 2500 nm and are coupled to a melamine aggregation inducing agent; mixing the test sample with the particles so as to allow melamine, if present in the test sample, to interact with the particles; monitoring the media to observe a change in color or turbidity; and then correlating changes in the color or turbidity of the media with the presence or absence of melamine in the test sample. In this way, the presence or absence of melamine in a test sample can be easily and rapidly observed. Moreover, various embodiments of the invention are highly sensitive. In certain embodiments of the invention, the range of melamine detection is between 10 ppb and 10 ppm.

Illustrative particles useful in the disclosed assays include gold nanoparticles (e.g. those having an average diameter of between 1 and 100 nm). As disclosed herein, the concentration of agents such as gold nanoparticles can be controlled depending upon the parameters of the specific assay. In some embodiments, the concentration of gold nanoparticles is between 1 and 100 nM). An illustrative aggregation inducing agent that can be coupled to the particles used in the invention is cyanuric acid (1,3,5-triazine-2,4,6-triol), a chemical compound having the formula $(CNOH)_3$ (CAS number 108-80-5). In additional to cyanuric acid, other compounds that can facilitate the aggregation of melamine and are useful with embodiments of the invention include acetic acid, oxalic acid, tannin, and chemicals possessing certain imide groups such as thymine, uracil, guanine, uric acid, riboflavin, barbituric acid, maleimide, succinimide, diacetamide, glutarimide and their derivatives.

As illustrated by the disclosure provided herein, there are a wide variety of illustrative embodiments of the invention. One specific illustrative embodiment of the invention is a method for detecting melamine in a liquid sample (e.g. water or milk) comprising mixing the liquid sample with a first reagent that extracts the melamine from the liquid sample; filtering the extractate through 0.45 µm filter; washing the resultant filtrate with a second reagent via liquid-liquid extraction; and then testing the upper aqueous solution for the presence of melamine by mixing it with a third reagent that forms a colorimetric reaction when exposed to melamine. In such embodiments of the invention, the first reagent can comprise dimethylformamide (DMF), methyl sulfoxide (DMSO), tetrahydrofuran (THF), acetonitrile, methanol, and mixtures of these compounds (e.g. in an aqueous solution). In embodiments of the invention, the second reagent can comprise chloroform, methylene chloride, alkyl halides or a mixture of these compounds. In certain embodiments of the invention, the second reagent further comprises an acidic aqueous solution. Optionally, the acidic aqueous solution comprises phosphoric acid, sulfuric acid, nitric acid, hydrogen halide, acetic acid, formic acid or mixtures of these agents. In such embodiments of the invention, the second reagent can comprise metallic nanoparticles disposed in an aqueous dispersion, for example gold nanoparticles having an average diameter of 5 nm, 10 nm, 15 nm, 20 nm, 30 nm, 40 nm, 50 nm, 60 nm, 70 nm, 80 nm, 90 nm, or 100 nm. In these embodiments of the invention, the metallic nanoparticles are functionalized with (e.g. covalently coupled to) an agent having an affinity for melamine, such as an anti-melamine antibody, a melamine aptamer, cyanuric acid and/or a cyanuric acid derivative, thymine and/or a thymine derivative, citrate, or mixtures of these agents.

Related specific embodiments of the invention include methods for detecting melamine in a solid sample (e.g. a milk powder such as is used in infant formulas). Optionally in such methods, the solid sample is subjected to one or more pretreatment steps, for example a mechanical processing step using a homogenizer, a pestle and mortar or the like. In these methods, the solid sample is mixed with a first reagent that extracts melamine from the solid sample. The resulting extractate is then filtered through a 0.45 µm filter. The resultant filtrate is then washed with a second reagent via a liquid-liquid extraction step. The upper aqueous solution is then tested for the presence of melamine by mixing it with a third reagent that forms a colorimetric reaction when exposed to melamine. In these embodiments of the invention, the first reagent can comprise dimethylformamide (DMF), methyl sulfoxide (DMSO), tetrahydrofuran (THF), acetonitrile, methanol, and mixtures of these compounds (e.g. in an aqueous solution). In these embodiments of the invention, the second reagent can comprise chloroform, methylene chloride, alkyl halides or a mixture of these compounds. In certain embodiments of the invention, the second reagent further comprises an acidic aqueous solution. Optionally, the acidic aqueous solution comprises phosphoric acid, sulfuric acid, nitric acid, hydrogen halide, acetic acid, formic acid or mixtures of these agents. In such embodiments of the invention, the second reagent can comprise metallic nanoparticles disposed in an aqueous dispersion, for example gold nanoparticles having an average diameter of 5 nm, 10 nm, 15 nm, 20 nm, 30 nm, 40 nm, 50 nm, 60 nm, 70 nm, 80 nm, 90 nm, or 100 nm. In these embodiments of the invention, the metallic nanoparticles are functionalized with (e.g. covalently coupled to) an agent having an affinity for melamine, such as an anti-melamine antibody, a melamine aptamer, cyanuric acid and/or a cyanuric acid derivative, thymine and/or a thymine derivative, citrate, or mixtures of these agents.

Figure 10A:
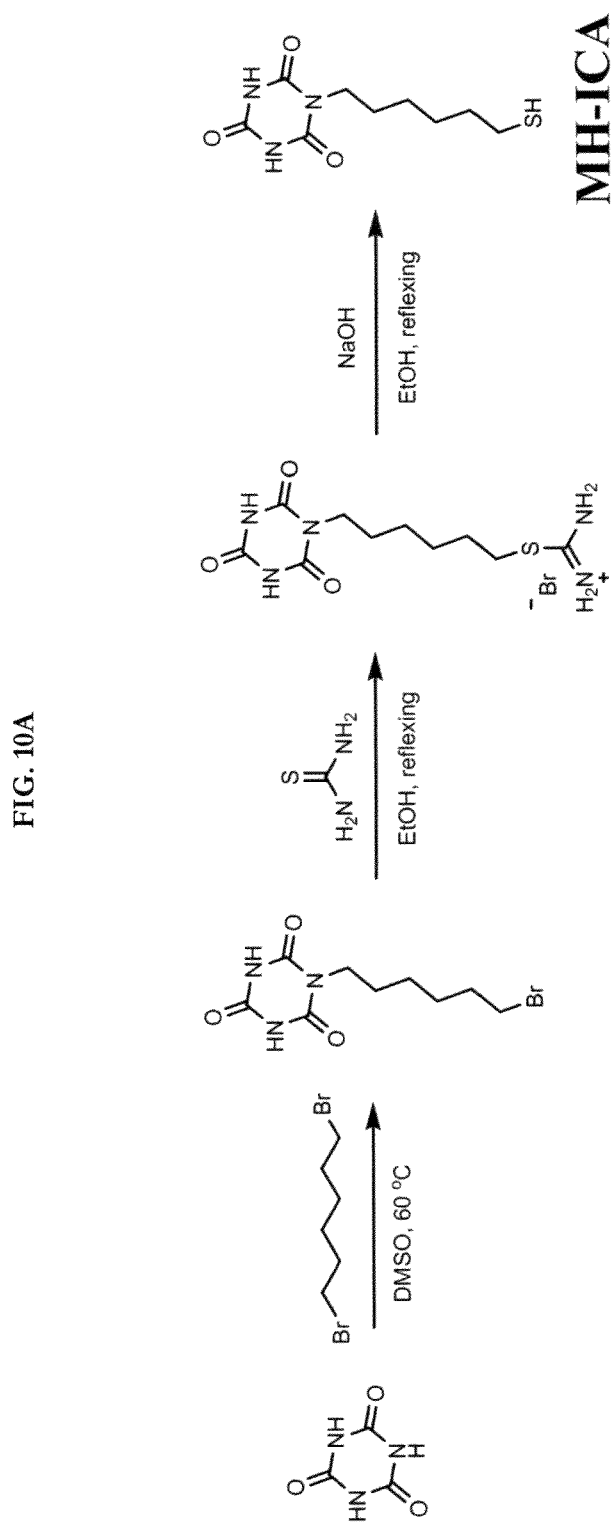
FIG. 10A provides an illustrative schematic for the preparation of Mercaptohexyl-isocyanuric acid (MH-ICA).

In the exemplary embodiment discussed in Example 2 below, cyanuric acid can be coupled to gold nanoparticles by making Mercaptohexyl Isocyanuric Acid (MH-ICA) as shown in FIG. 10A, and then adding this MH-ICA solution to a suspension of 1 mL Au NPs leads to form MH-ICA/NPs. While the disclosure in Example 2 provides an illustrative methodology, a variety of methods and materials are known in the art that can be used to couple an aggregation inducing agent to a particle including those disclosed in Agasti et al., J. Am. CHEM. SOC. 2009, 131, 5728-5729; Daniel et al., J. Am. Chem. Soc., 2009, 131 (18), pp 6362-6363; and Ai et al., J. Am. Chem. Soc., 2009, 131 (27), pp 9496-9497, the contents of which are incorporated by reference.

Figure 11:
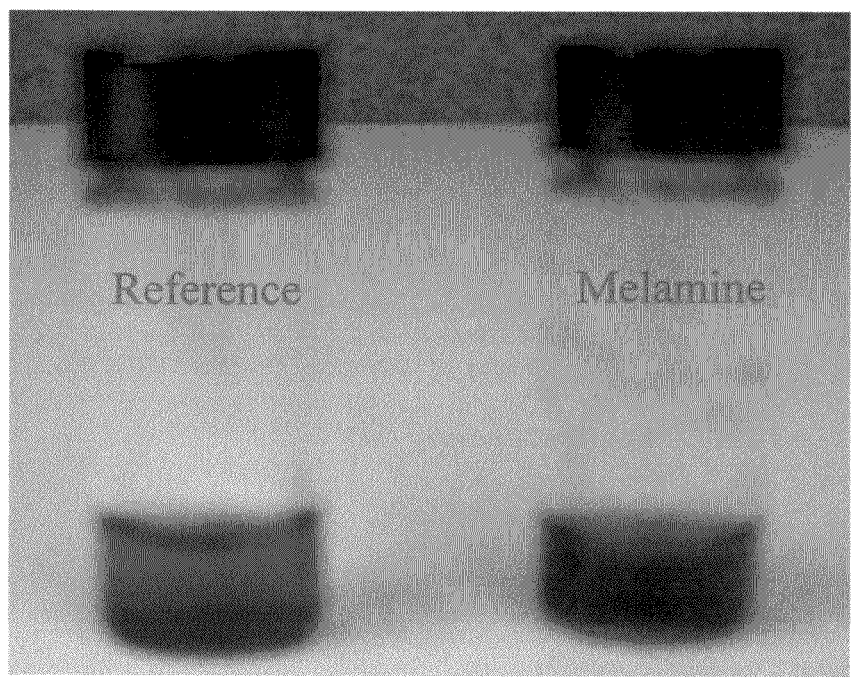
FIG. 11 provides a photograph of metallic nanopartides coupled to cyanuric acid in the absence and presence of melamine. The color of the metallic nanoparticle solution changed from red to black in the presence of melamine.
Figure 12:
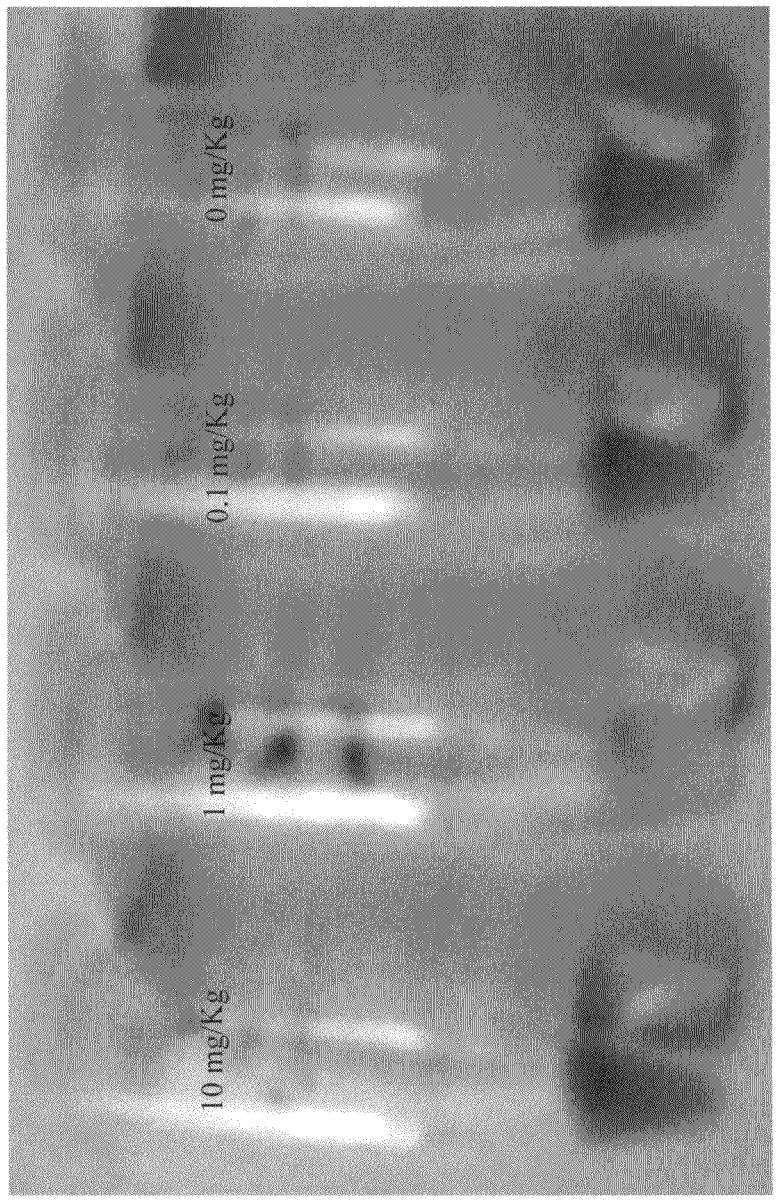
FIG. 12 provides a photograph of 100 μL of solutions of metallic nanoparticles coupled to cyanuric acid upon the addition of 1 μL of melamine solution with the concentrations of 0 mg/kg, 0.1 mg/kg, 1 mg/kg and 10 mg/kg.

A variety of methods and materials can be used in the disclosed methods for the detection of melamine. In the demonstration of these methods that is shown in FIG. 11, an aqueous solution of metallic nanoparticles was added to a melamine saturated solution. This resulted in the color of the metallic nanoparticle solution changing from red to black (FIG. 11). Moreover, in these assays, the colorimetric change of metallic nanoparticle solution corresponds to the concentration of added melamine. For example, in the illustration of these methods that is shown in FIG. 11, 100 μL of metallic nanoparticle solutions were added to 1 μL samples of melamine solution with the concentrations of 0.1 mg/kg, 1 mg/kg, 10 mg/kg and 100 mg/kg. This resulted in the color of the metallic nanoparticle solution changing from yellow, to yellowish pink, light pink and violet blue (FIG. 12). Without being bound by a specific scientific theory or principle, the color change of metallic nanoparticles is believed to occur by the aggregation of metallic nanoparticles induced by melamine.

Figure 13:
FIG. 13 provides a photograph of 100 μL of metallic particles (gold nanoparticles coupled to cyanuric acid) solution upon the addition of the commercial milk with and without melamine contamination.

To demonstrate the ease in the practical implementation of embodiments of the invention, commercially available milk with and without melamine contamination was assayed. As shown in FIG. 13, the color change of metallic nanoparticle solution is negligible with milk without melamine contamination. In contrast, the yellowish metallic nanoparticle solution turned to pink after exposure to milk intentionally contaminated with 1 mg/kg of melamine. In summary, the colorimetric diagnosis of melamine contamination in milk using metallic nanoparticles coupled to a melamine aggregation inducing agent has been demonstrated. Moreover, embodiments of these methods allow the visual detection of a concentration of melamine in milk that is below 2.5 mg/kg, the safety limit for the consumption of melamine in adults as set by FDA regulations. Further illustrations of such embodiments of the invention are disclosed in the Examples below.

As shown by the data in Example 2, in typical embodiments of the invention, the detection process is carried out by the naked eye without the need for assisting instrumentation (e.g. spectrometers and the like). However, certain embodiments of the invention can use assisting instrumentation, for example a spectrometer such as one used in mass spectroscopy, Raman spectroscopy, enzyme-linked immunosorbent assays, chemiluminescent assays and the like (See, e.g. Rovner, S. L. Chem. Eng. News 2009, 87, 36-38; U.S. FDA Laboratory Information Bulletin No 4421; Zhu et al., Chem. Commun. 2009, 559-561; Huang et al., Chem. Commun. 2009, 556-558; Lin et al., J. Food Sci. 2008, 73, T129-T134; He et al., Sens. Instrumen. Food Qual. 2008, 2, 66-71; Garber, E. A. E. J. Food Prot. 2008, 71, 590-594; and Wang et al., J. Agric. Food Chem. 2009, 57, 3464-3469). GC-MS and LC-MS protocols are recommended by the Food and Drug Administration (FDA) as standard analytical methods for the detection of melamine.

The following examples are given to aid in understanding the invention, but it is to be understood that the invention is not limited to the particular materials or procedures of these examples.

EXAMPLES

Example 1

Methods and Materials for the Detection of Melamine Using Particles Such as Gold Nanoparticles In the assays described in Example 1 the aggregation-forming chemical compound (cyanuric acid) is not coupled to particles.

Illustration of the Simplicity of Typical Detection Protocol Methods

1. Mix nanoparticles with the test sample.
2. Add the precipitation-inducing chemical into the nanoparticle/sample mixture.
3. Measure the colorimetric and turbidimetric change of the solution with a spectrometer or by the naked eye.

Example

Protocol Used to Obtain the Data Included in the Patent Description

|  |  | Concentration | Volume (ul) | Source |
|---|---|---|---|---|
| Nanoparticle | 10 nm gold nanoparticles | 0.01% Au | 80 | Sigma |
| Precipitation-inducing chemical | Cyanuric acid | 2000 ug/ml | 40 | Sigma |
| Samples spiked with melamine | Melamine | 2000~0.5 ug/ml | 80 | Sigma |

Effects of Modulating NP Concentration on Detection Sensitivity

Figure 4A:
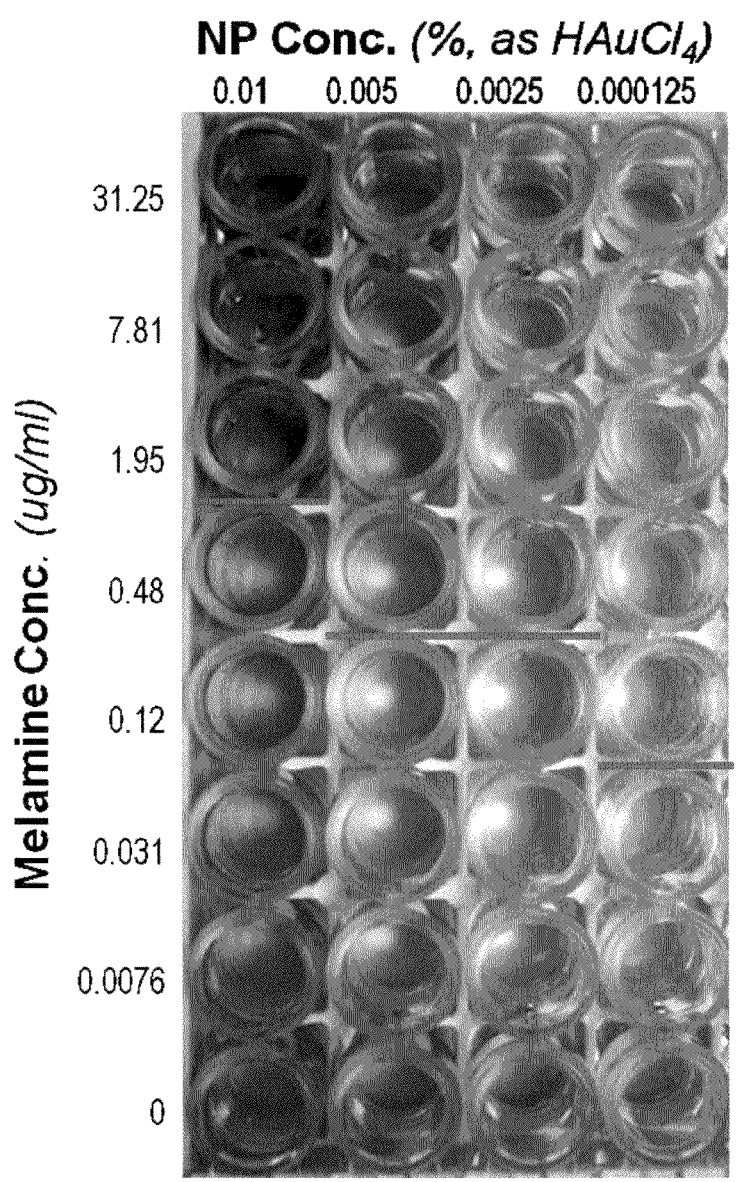
FIGS. 4A and 4B provide photographs showing the detection melamine in water with NP of different concentrations A) before and B) after addition of cyanuric acid. The red lines indicate the detection cut-off with observations via the naked eye. In these assays, the cyanuric acid (precipitation-inducing compound) was not coupled to the nanoparticles.
Figure 4B:
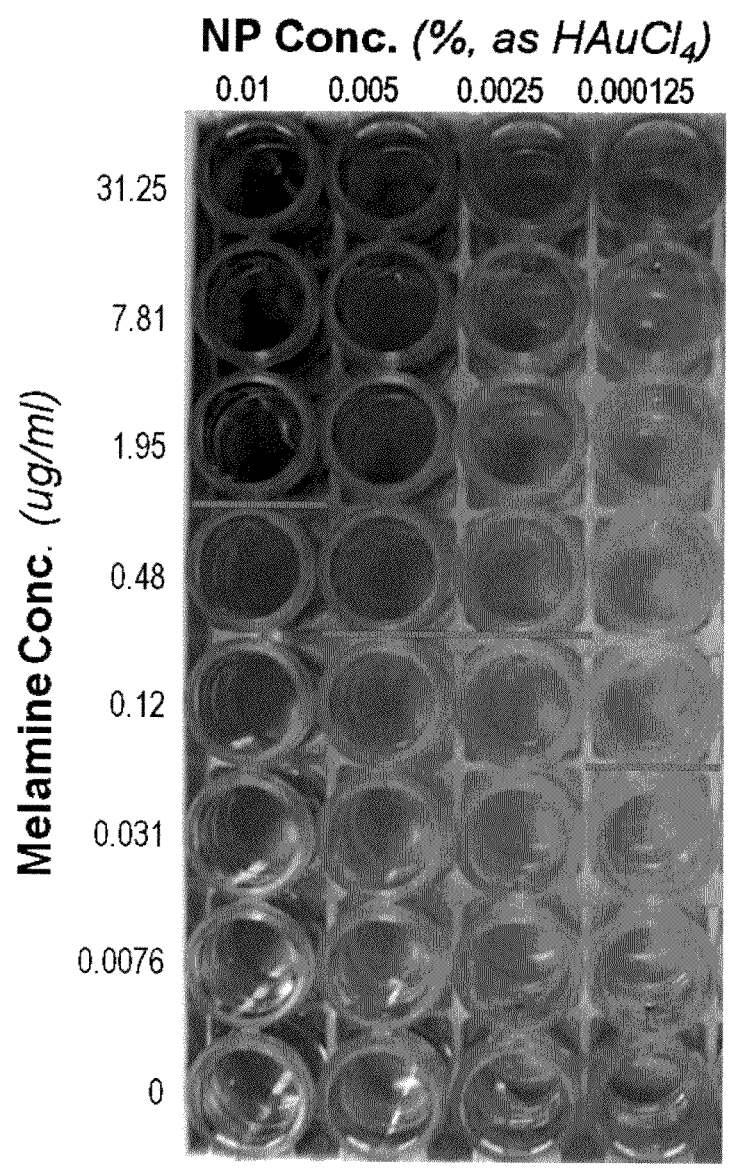

In illustrative embodiments of the invention, 80 ul NP (10 nm gold nanoparticles) is mixed with 80 ul sample containing different concentrations of melamine, followed by addition of 40 ul precipitation-inducing chemical (2000 ug/ml cyanuric acid). Pictures taken before and after addition of cyanuric acid are shown in FIGS. 4A and 4B. As shown by the data in this figure, the lower the NP concentration, the less melamine will be required to induce the color change, thus the better the detection sensitivity. The sensitivity with 0.000125% NP is 16 times better than that with 0.01% NP. However, if the NP concentration is too low, the color may be too light to be directly seen by human eyes, and the use of assisting instrumentation may therefore be warranted.

The colorimetric change of nanoparticles (NPs) upon addition of melamine is due to the aggregation of NPs. Therefore, any experimental parameters that can change the tendency of NPs to aggregate can be modulated to affect the sensitivity of the detection method. In addition to the NP concentrations, other parameters such as pH, ionic strength, size and surface charge density of NPs can also be used to modulate the sensitivity of an assay.

Use of UV-Visible Absorbance Spectrometer in the Detection of Melamine

Figure 5A:
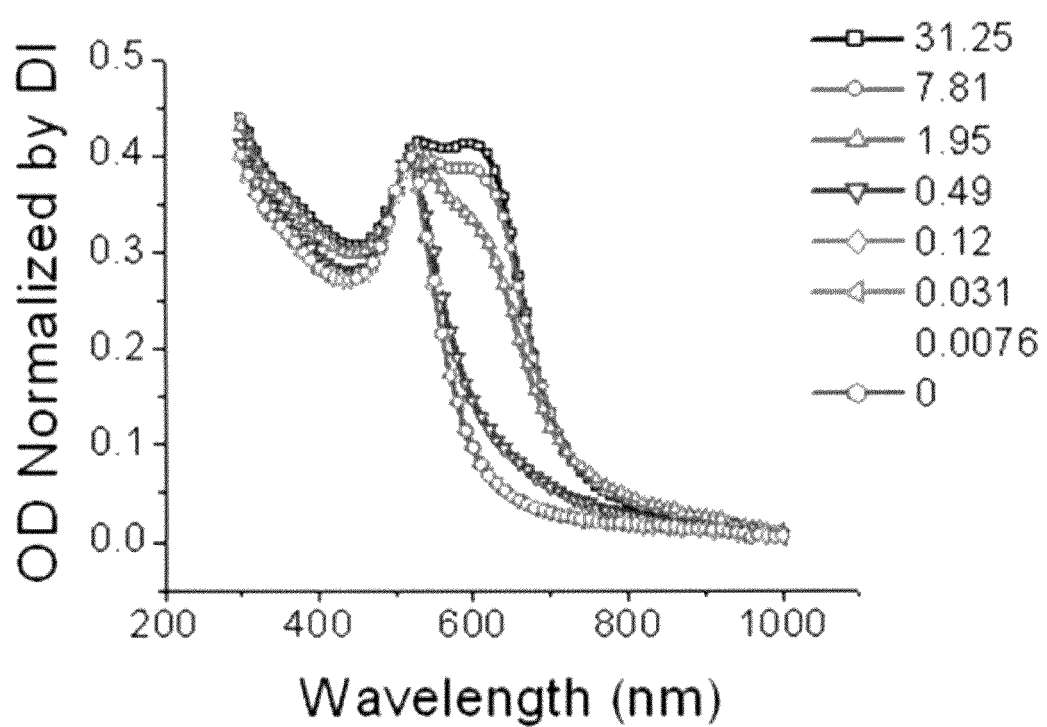
FIGS. 5A and 5B provide data collected with UV-visible spectrometer: Absorbance spectrum before (A) and after (B) addition of cyanuric acid.
Figure 5B:
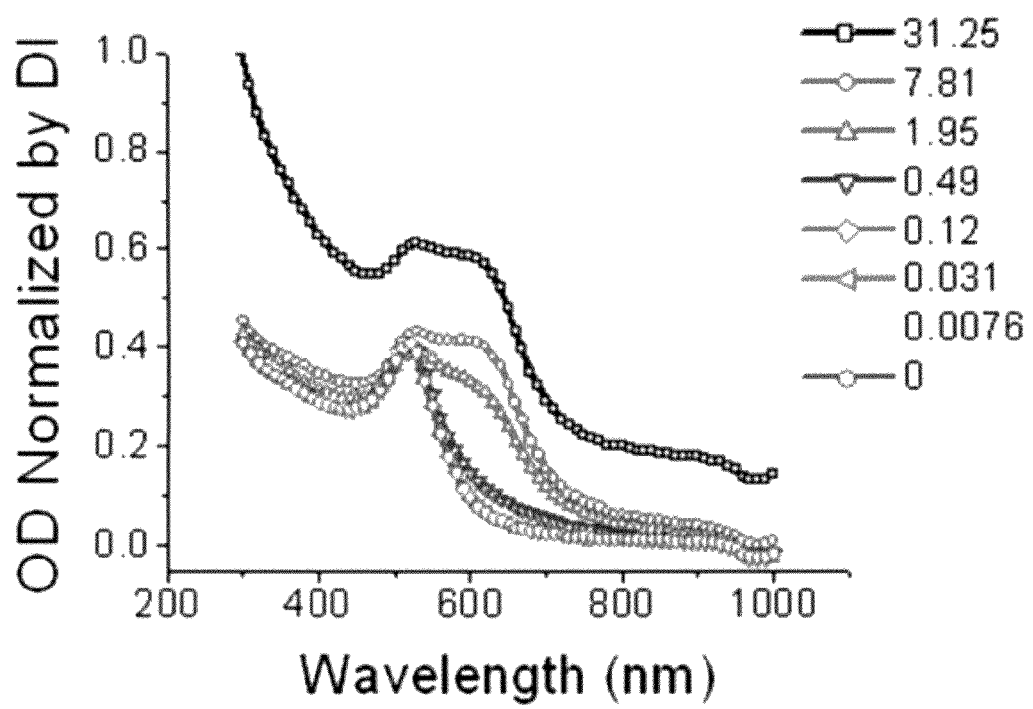
Figure 5C:
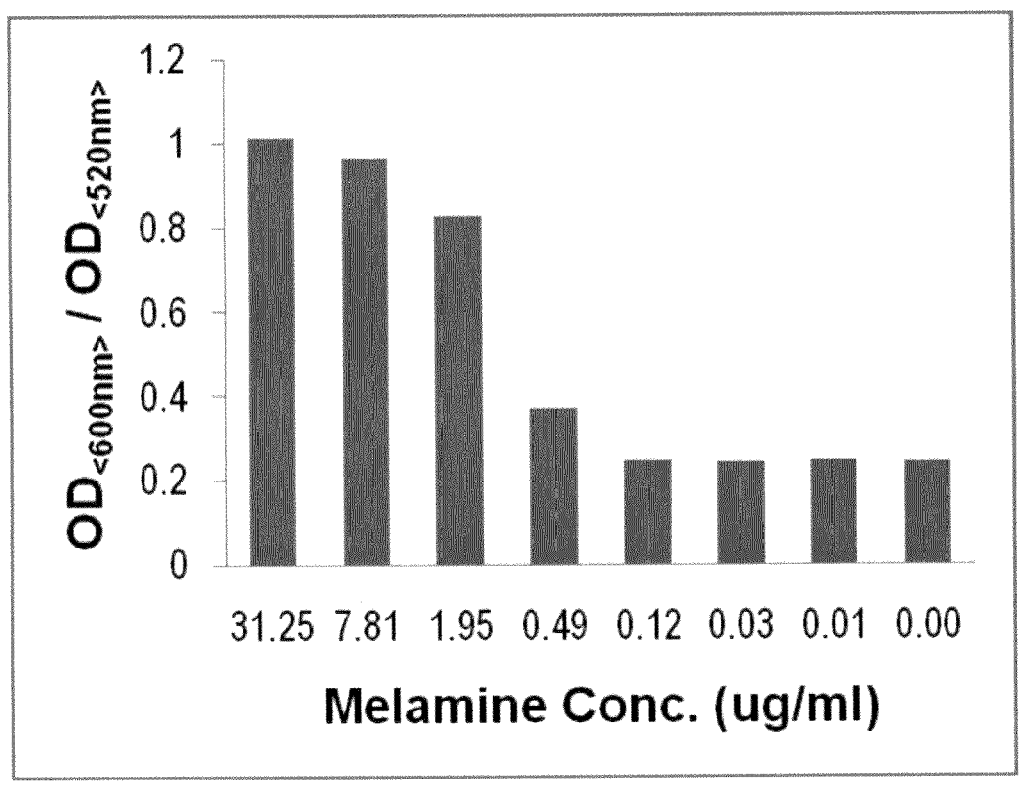
FIGS. 5C and 5D provide colorimetric change before addition of cyanuric acid (C) and turbidimetric change after addition of cyanuric acid (D) measured by spectrometer. The spectrometer data shown here is from the first column of FIG. 4 (80 ul 0.01% 10 nm gold nanoparticle with 80 ul melamine sample, with or without 40 ul cyanuric acid). In these assays, the cyanuric acid (precipitation-inducing compound) was not coupled to the nanoparticles.
Figure 5D:
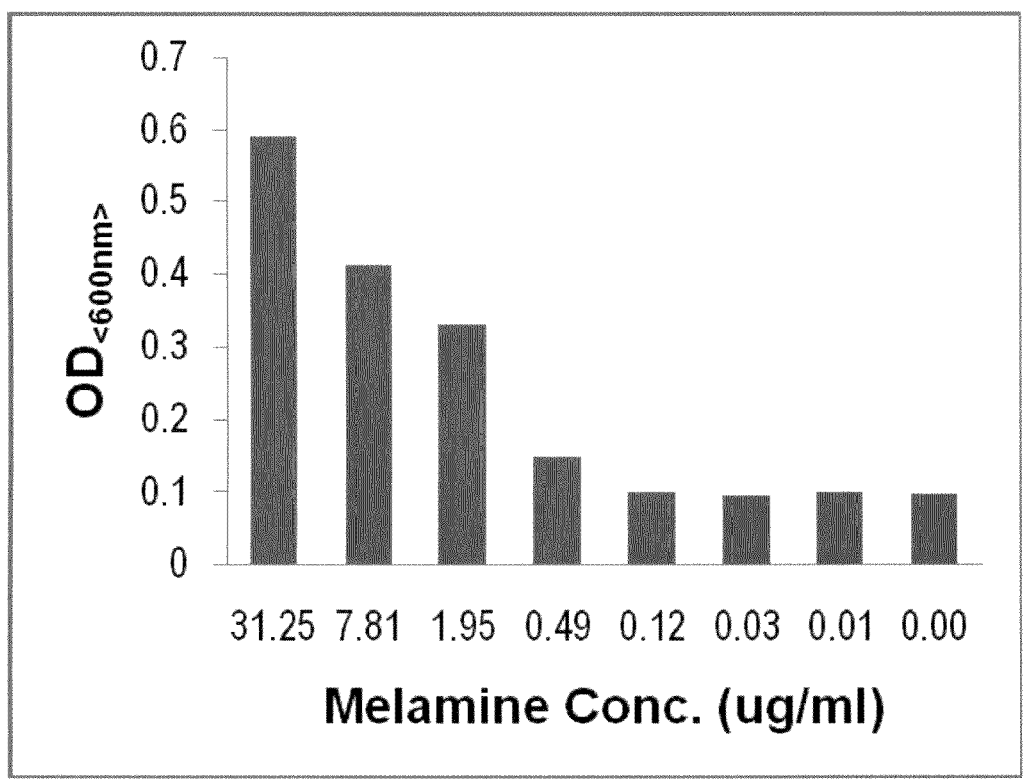

For the first column in the FIGS. 4A and 4B where detection cut-off by the naked eye is about 2 ug/ml, the absorbance was measured with a UV-visible spectrometer. The results are provided in FIGS. 5A, 5B, 5C, and 5D. In FIGS. 5A, 5B, 5C, and 5D, a red shift is observed in the absorbance spectrum whether or not cyanuric acid is added. This disclosure shows that the observed color change is due to the interaction between melamine molecules and NPs, and that this interaction can occur in the absence of an aggregation inducing agent such as cyanuric acid. The increased absorbance while cyanuric acid is added indicates the formation of insoluble melamine-cyanuric acid aggregation/precipitation complex. As shown in FIGS. 5(C) and (D), both colorimetric and turbidimetric change observed with the naked eye can be quantified, in a more detailed way, for example by quantifying absorbance data using a spectrometer. In this example, compared to observations via the naked eye, the absorbance spectrometer has improved the detection limit by 5 fold (from 2 ug/ml to 0.5 ug/ml).

As disclosed herein, it is possible to generate a significant change in NP complex size upon addition of melamine (changing from tens of nm to hundreds of nm), a change which results in an observable signal. For NPs, the color observed is due to both light absorbance and light scattering. In this context, mechanical observations of light absorbance, such as those using the UV-visible spectrometer, as well as mechanical observations of light scattering such as those using a turbidimeter, can be used to increase the sensitivity of embodiments of the invention. Light scattering based detection methods, for example hyper-Rayleigh scattering and/or differential light-scattering spectroscopy can be used to monitor very faint color changes (see, e.g. Bogatyrev et at, Colloid Journal, 2002, 64(6), 671-680). In scattering based spectroscopy, the scattering amplitude of resonance typically depends on the color of the NPs, a property which comes from the surface plasmon resonance of the NPs. Consequently, in such embodiments, a response according to the color change of NPs can be amplified so that the sensitivity of the assay is enhanced. Moreover, both resonance and light scattering properties are functions of NP size, i.e. the color of the NPs. For example, in certain embodiments, a 100 nm particle size change will result in about 60 nm resonant wavelength shift. Consequently, in certain embodiments of the invention, the detection sensitivity can be increased by modulating in the particle size in combination with light absorption and/or scattering equipment and technologies.

Modulating Melamine Assay Detection Parameters Sensitivity and Dynamic Range

In certain embodiments of the invention, the colorimetric signal associated with the interaction between melamine and the AuNPs is due to the formation of AuNP aggregates. Therefore, the sensitivity and dynamic range of the colorimetric signal may be dependent on the resistance of AuNP to aggregation and can be adjusted by changing the buffer composition of the AuNPs. To demonstrate this, the effect of NaCl, which is well-known to destabilize the AuNPs, was investigated.

Figure 6A:
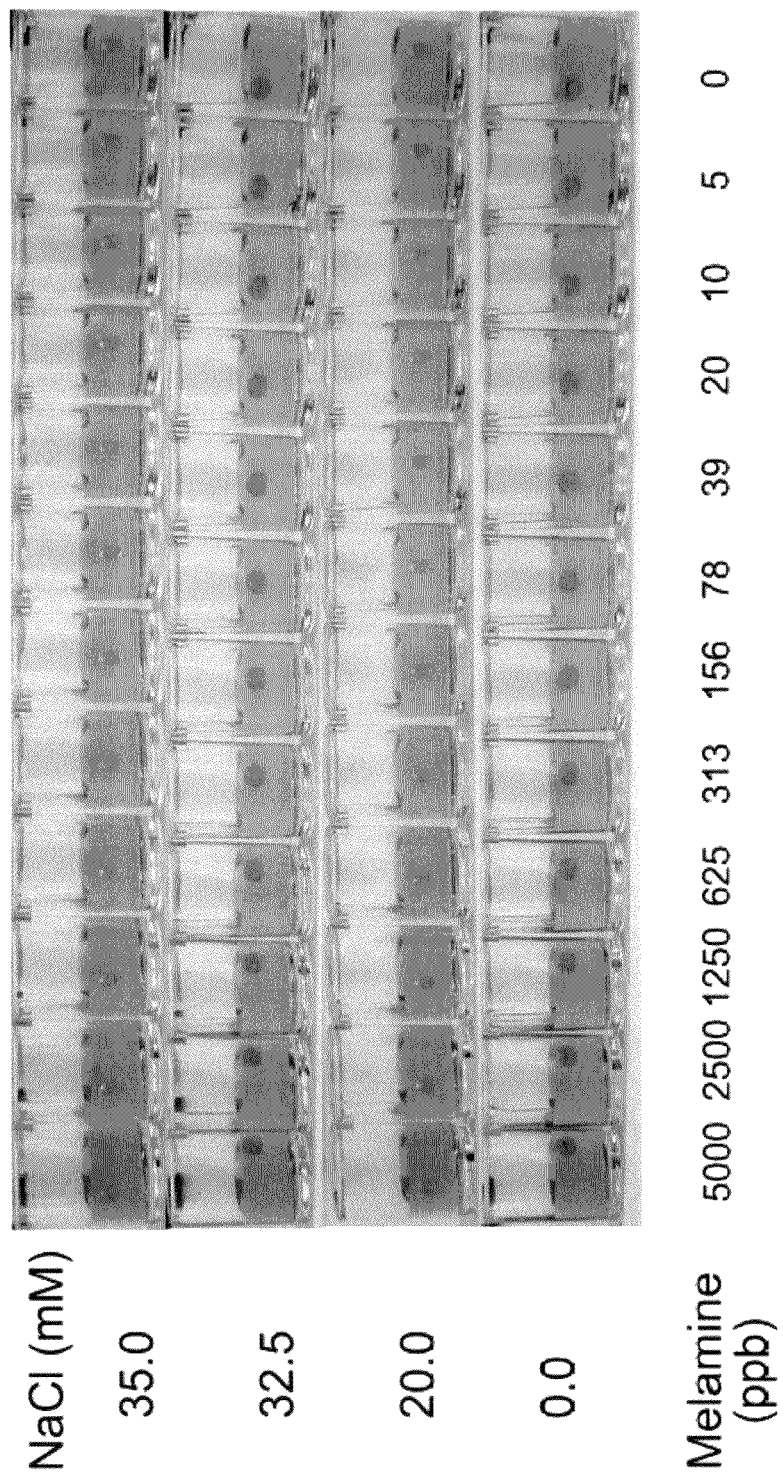
FIGS. 6A and 6B provide photographs (A) captured by a digital camera and (B) the ratio of absorbance readings at 660 nm to that at 518 nm versus the melamine concentrations in the presence of NaCl. 30 μl from each melamine sample was mixed with 30 μl AuNP (~0.005% HAuCl4) solution containing NaCl of different concentrations.
Figure 6B:
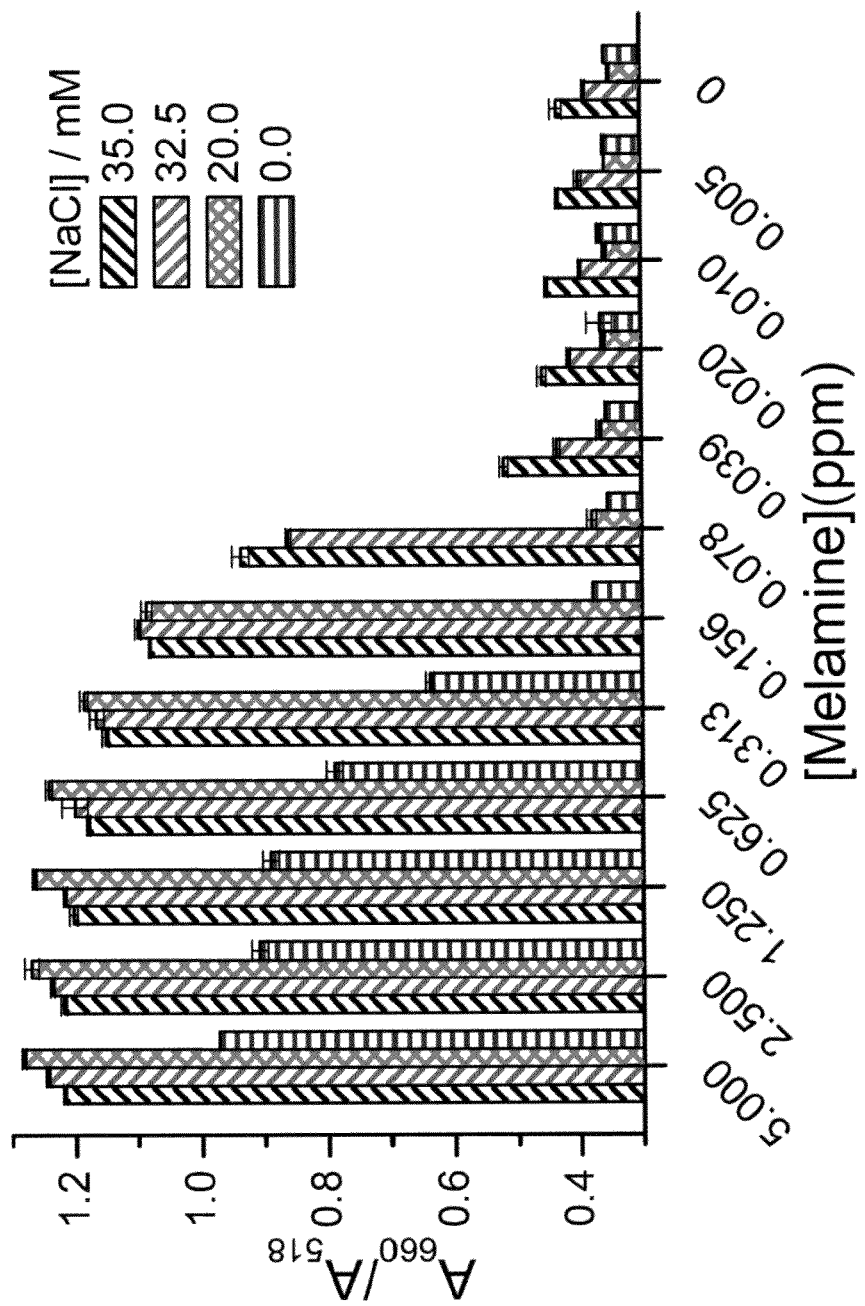

In these studies, AuNPs were premixed with NaCl of different concentrations and the resulting mixtures were used to detect melamine (FIGS. 6A and 6B). As expected, a different sensitivity and dynamic range was observed for AuNP aqueous medias containing different concentrations of NaCl. For example, a significant color change occurred between 78 ppb and 39 ppb for AuNPs with 35 mM NaCl whereas a color change occurred between 313 ppb and 156 ppb for AuNPs without NaCl. Here, with NaCl as an example, it is demonstrated that it is possible to adjust the detection sensitivity and dynamic range to a desired concentration range by the addition of AuNP destabilizing/stabilizing reagents.

The adjustability in sensitivity and dynamic range is very valuable for practical applications of embodiments of the invention in the variety different contexts in which melamine can be detected. For example, particles such as AuNPs and/or the aqueous media in which they are mixed, can be pre-conditioned (e.g. by controlling particle size, the pH of the particles and/or of the assay media, their salt concentrations, their buffer conditions and the like) so that a significant color change occurs at a predetermined melamine concentration threshold (e.g. a threshold safety level of 2.5 ppm or 1 ppm etc.). In an illustrative example of such embodiments of the invention, if no color change is observed in the pre-condition assay media after its combination with the test sample, this indicates the absence of melamine in the test sample and/or the presence of melamine in the test sample at a concentration below 2.5 ppm. Alternatively; if a color change is observed, this indicates the presence of melamine in the test sample at a concentration above 2.5 ppm. In certain embodiments, an aggregation inducing agent such as cyanuric acid can included with the assay media to increase the specificity of the assays.

Figure 7A:
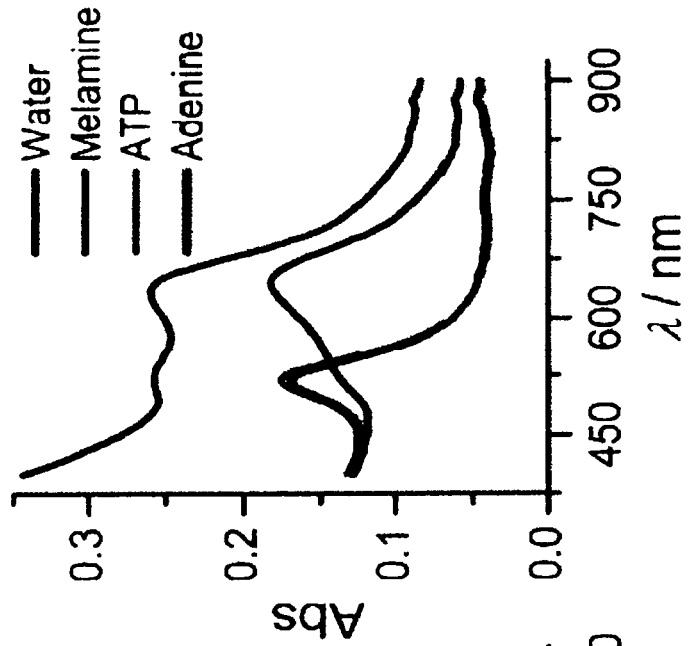
FIGS. 7A and 7B provide UV-vis spectra of AuNP (black) and the mixtures containing melamine (red), ATP (green), and Adenine (blue) in the absence (A) and presence (B) of cyanuric acid. AuNP concentration=0.5A520 units/ml (~0.005% HAuCl4), melamine concentradon=0.5 mM (~62.5 ppm), ATP concentration=0.5 mM, adenine concentration=0.5 mM, and cyanuric acid concentration=400 ppm. In the assays shown in FIG. 7B, the cyanuric acid (precipitation-inducing compound) was not coupled to the nanoparticles.
Figure 7B:
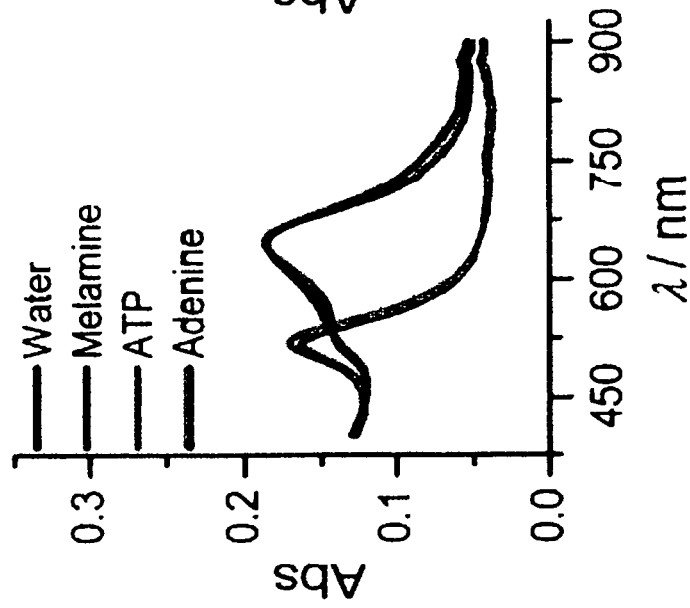

Use of Aggregation Inducing Agents Such as Cyanuric Acid to Increase Assay Specificity In certain embodiments of the invention designed to examine the specificity of colorimetric changes of the AuNPs, additional control molecules containing exocyclic amines were also mixed with AuNPs. As seen from absorbance spectra in FIG. 7A, a dramatic red shift was observed for melamine while no shift was observed for ATP of the same concentration. This indicates that the colorimetric signal shows great selectivity for melamine over some amine-baring molecules such as ATP which are shown to be insufficient to induce significant color changes to the same degree as that observed with melamine. However, some structurally similar molecules, such as adenine, were shown to be able to induce a similar red-shift as melamine. Therefore, cyanuric acid, which is known to form precipitates with melamine via highly specific hydrogen bonds (see, e.g. Seto et al., Journal of the American Chemical Society, 1990, 112, 6409-6411), was then introduced in the detection. A comparison of FIGS. 7A and 7B show that the addition of cyanuric acid leads to a significant change in the absorbance spectra only for melamine. With colorimetric output from AuNPs and precipitation from cyanuric acid, a dual selectivity is achieved without involving any modifications on either the AuNP or cyanuric acid.

Detection of Melamine in Whole Milk

Milk is a complex system and its various components serve as potentially interactive species with melamine regardless of detection methodology (e.g. LC-MS, GC-MS, ELISA or colorimetric detection). Conventional assays for melamine detection in milk usually require complicated and time-consuming separation steps, including acetonitrile extraction and/or ion pair chromatography, steps which can severely hinder the application of on-site detections of melamine in milk and other foodstuffs.

Figure 8:
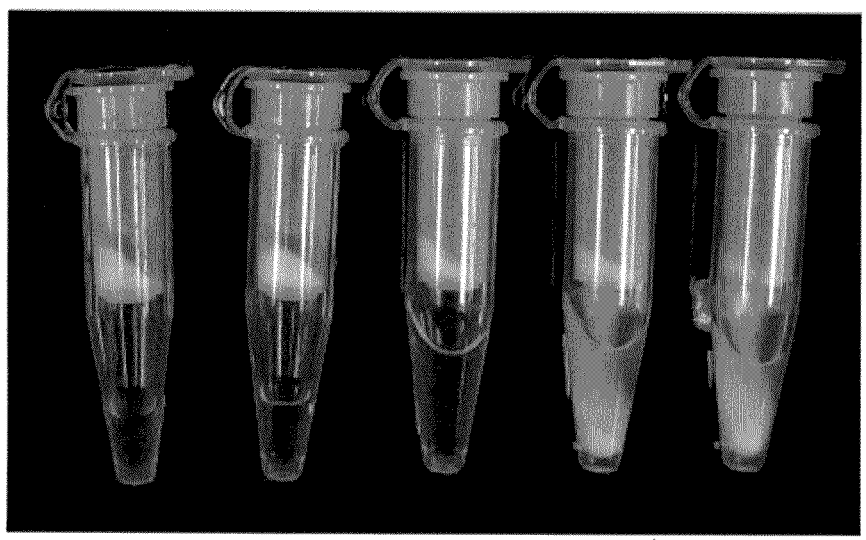
FIG. 8 provides a photograph showing milk separations at different pH. (1) pH<0, (2) pH 3-4, (3) pH 5-6, (4) pH 6-7, (5) pH 7. Upper panel: Spiked milk after centrifuge at 10,000 rpm for 10 min. Lower panel: pH test paper results of the spiked milk.
Figure 8:
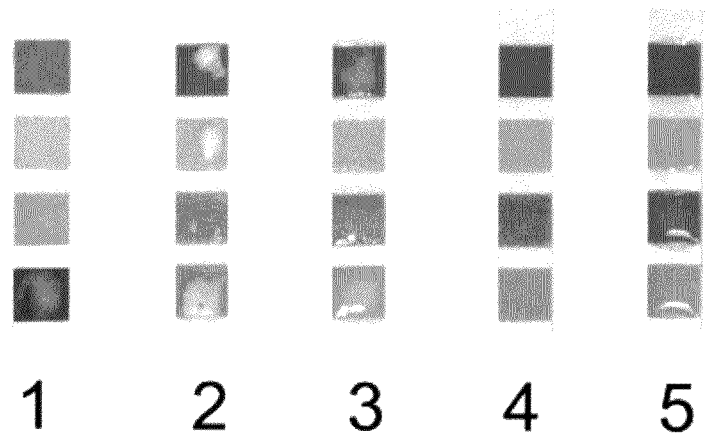
Figure 9A:
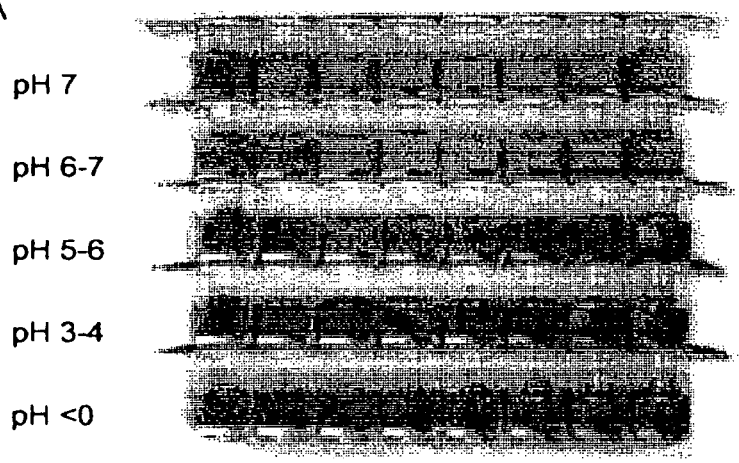
FIGS. 9A and 9B provide data from assays designed for the detection of melamine in milk after separation. (A) Visual color and turbidity changes of serials concentration of melamine under separation condition with different pH. (B) The colorimetric concentration profile (O.D. 660 nm/518 nm) with pH 3-4. The dotted line indicates the negative control. The concentrations of melamine spiked into milk are (from left to right) 1600, 400, 100, 25, 6.25, 1.56, 0.39, 0 ppm.
Figure 9B:
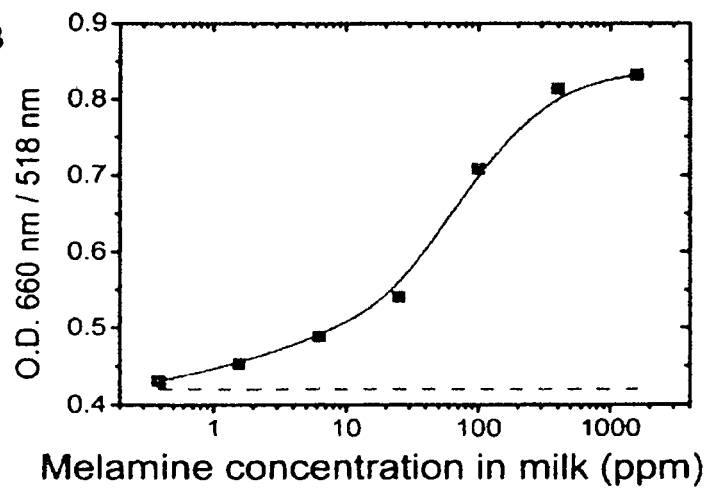

To illustrate a practical embodiment of the invention, a rapid strategy to extract melamine from milk was designed. In FIGS. 9A and 9B, five different concentrations of HCl were added into the spiked milk, resulting in pH values of 7, 6-7, 5-6, 3-4, <0. A white jelly precipitation was generated immediately. 500 μL of the mixtures was transferred into different filtration tubes (Millipore, USA, pore size 5 μm), followed by centrifugation at 10,000 rpm for 10 minutes. In order to avoid filtration tube blockage from the precipitants in the milk, a pore size>=5 μm was used. After that, the transparent liquid component were transferred for subsequent detection (FIG. 8). Similar to the results observed with DI water, a high concentration of melamine resulted in both blue color and precipitation. Conversely, a low concentration of melamine resulted in a transparent and red-colored sample. The modulation of pH was also observed to influence the detection process. As shown in FIG. 9A, a low pH (pH<6) resulted in effective separation of milk and resultant increase in detection sensitivity. With an optimized pH level of around 3-4, both color and turbidity changes can be observed above the 0.4 ppm melamine concentration (FIG. 9B). The detection methodology used in this embodiment of the invention, one which included the acid-based milk component separation step as well as the visual observation of color and turbidity changes, was completed in less than 15 minutes.

Example 2

Methods and Materials for the Detection of Melamine Using Particles Coupled to a Compound Known to Facilitate Melamine Precipitation/Aggregation In the assays described in Example 2, the aggregation-inducing chemical compound (cyanuric acid) was coupled to particles prior to performing these assays.

Mercaptohexyl-isocyanuric acid (MH-ICA) is a typical agent useful for the surface functionalization of Au NPs. It is synthesized starting first with the alkylation of cyanuric acid to produce 6-bromohexyl isocyanuric acid (see FIG. 10A). Subsequent conversion to MH-ICA is achieved by thiolation with thiourea followed by hydrolysis with NaOH in ethanol. Detailed synthetic procedures and characterization data are provided in the Supporting Information below.

Figure 10B:
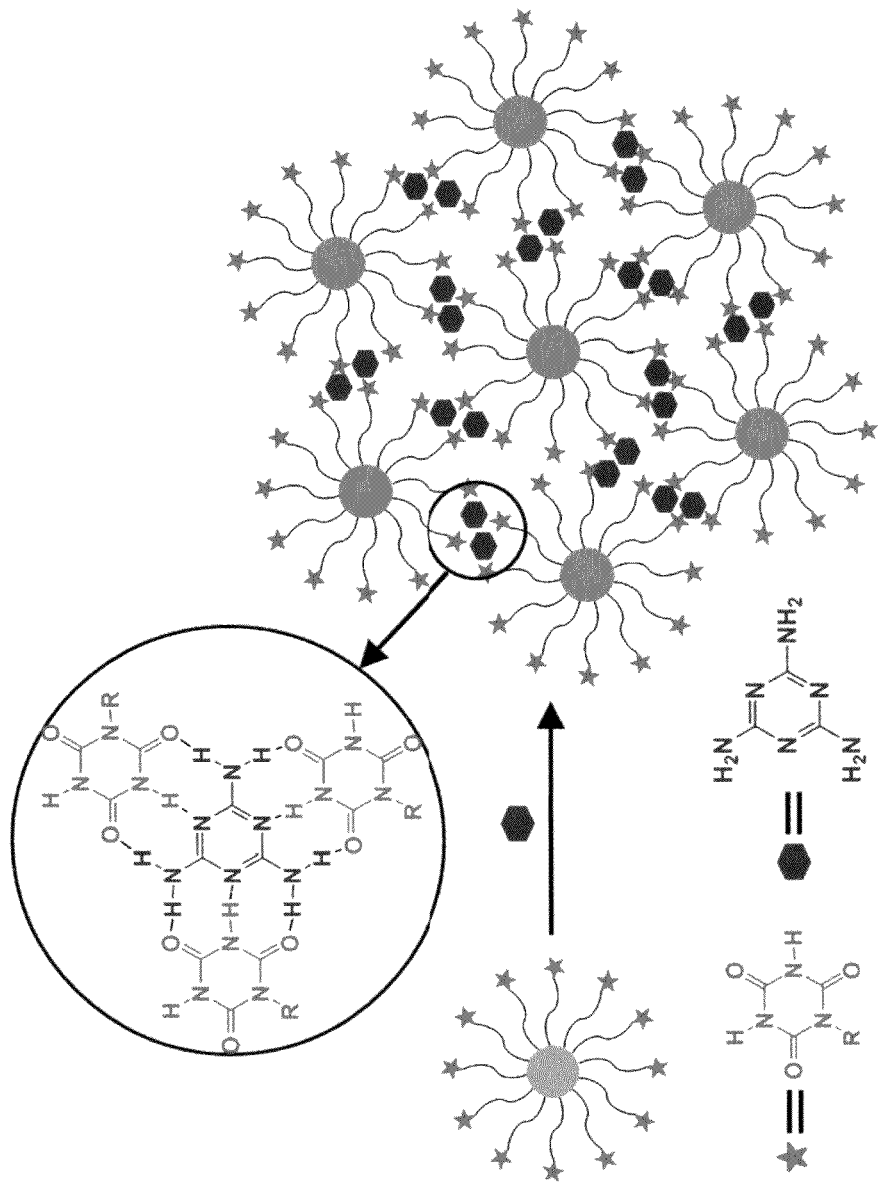
FIG. 10B provides an illustrative schematic showing multiple hydrogen bonding interactions between melamine (blue) and isocyanuric acid (red) which are believed to induce the aggregation of MH-ICA surface functionalized nanoparticles (MH-ICA/NPs). In this schematic, molecular and nanoparticle components are not drawn to scale.
Figure 14:
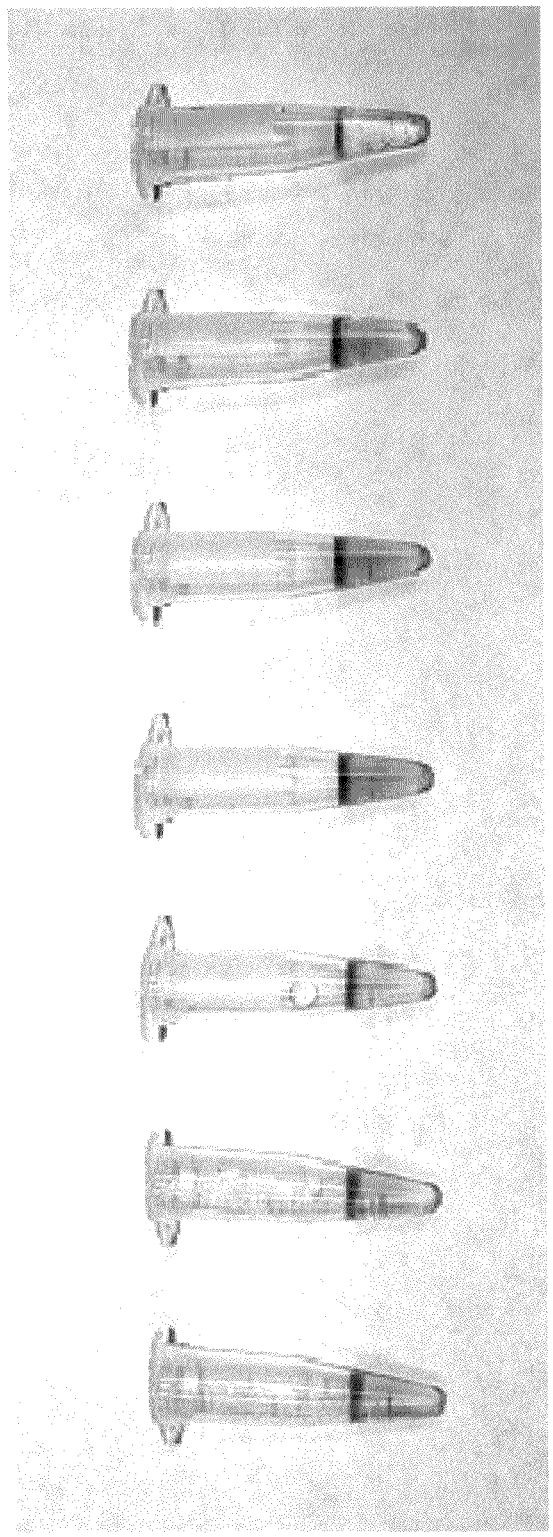
FIG. 14 provides a photograph of MH-ICA/NP dispersions after melamine addition. From left to right, the melamine concentrations are 0, 0.01, 0.1, 1, 10, 100, 1000 ppm by weight.

In this embodiment of the invention, Au NPs were synthesized following Frens' method (see, e.g. Frens, G. Nature Phys. Sci. 1973, 241, 20-22), resulting in ~10 nM solutions with an average particle diameter of ~13 nm, as determined by monitoring the absorbance at 520 nm. MH-ICA was added to these solutions under weakly basic conditions (pH=9) at a stoichiometric molar ratio of 500/1 to yield surface functionalized NPs (MH-ICA/NPs). Purification was achieved via centrifugation followed by redispersion in deionized water. The final coverage of MH-ICA on the NP surfaces was not quantified. As shown in FIG. 14, MH-ICA/NP suspensions in aqueous media are red, as a result of the surface plasmon absorbance being centered at ~520 nm. Addition of standard stock solutions of melamine having concentrations ranging from 0.01 ppm to 1000 ppm to MH-ICA/NP suspensions cause color changes from red to pink, then to purple (with increasing melamine concentrations). When melamine concentration is above 1000 ppm, the solutions become colorless, which is attributed to the precipitation of NP aggregates. The color change of the MH-ICA/NPs is due to the formation of multiple NP aggregates brought together as a result of specific H-bonding between melamine and cyanuric acid (see, e.g. Whitesides et al., Acc. Chem. Res. 1995, 28, 37-44; and Seto et al., J. Am. Chem. Soc. 1993, 115, 1330-1340). A schematic representative of overall aggregation-induced change in absorption is illustrated in FIG. 10B.

Figure 15A:
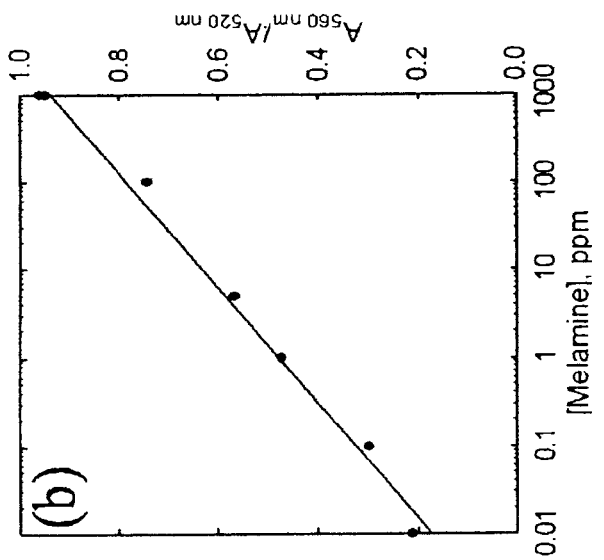
FIG. 15A provides UV-Vis absorption spectra of 200 μL MH-ICA/NP dispersions in water upon addition of 2 μL melamine stock solutions. Black, 0 ppm; blue, 0.01 ppm; green, 0.1 ppm; cyanine, 1 ppm; dark green, 5 ppm; dark blue, 100 ppm; red, 1000 ppm.

FIG. 15A shows the UV-Vis absorption spectra of MH-ICA/NP in water and after addition of melamine. This data shows a broadening of the plasmon absorption and a progressive shift in the maximum from 520 nm to 540 nm with continuous melamine addition. The red shift in absorption, together with the decrease and broadening of the extinction is consistent with a change in the number of interacting nanoparticles rather than a decrease in the internanoparticle distance (see, e.g. Rosi, et al., Chem. Rev. 2005, 105, 1547-1562; Wilson, R. Chem. Soc. Rev. 2008, 37, 2028-2045; Storhoff et al., J. Am. Chem. Soc. 1998, 120, 1959-1964; Storhoff et al., J. Am. Chem. Soc. 2000, 122, 4640-4650; Jain et al., J. Phys. Chem. B 2006, 110, 136-142; Liu et al., J. Am. Chem. Soc. 2003, 125, 6642-6643; Lee et al., Angew. Chem., Int. Ed. 2007, 46, 4093-4096; Daniel et al., A. J. Am. Chem. Soc. 2009, 131, 6362-6363; Jiang, et al., Angew Chem. Int. Ed. 2008, 47, 8601-8604; Elghanian et al., Science 1997, 277, 1078-1081; Nam et al., J. Am. Chem. Soc. 2002, 124, 3820-3821; and Medley et al., Anal. Chem. 2008, 80, 1067-1072). A plot of the ratio of the absorbance at 620 nm to that at 520 nm (A620/A520) against the log melamine concentration gives a linear curve (FIG. 15B), and can be used as an empirical calibration curve (see, e.g. Jiang, et al., Angew Chem. Int. Ed. 2008; Taton et al., Science 2000, 289, 1757-1760; Nie et al., Anal. Chem. 2006, 78, 1528-1534; Tsai et al., Microelectron. Eng. 2005, 78-79, 546-555; and Bui et al., Anal. Bioanal. Chem. 2007, 388, 1185-1190).

In order to show for example, the robustness of embodiments of the invention, a series of control experiments were carried out to demonstrate the specificity of the MH-ICA/NP aggregation to melamine. As provided in the Supporting Information, there is no variation in the absorption characteristics of MH-ICA/NP dispersions in the presence of up to 1000 ppm ammonia, hydroxylamine, hydrazine, urea or ethylene diamine. Subsequent addition of melamine to these solutions leads to a color change from red to purple, similar to that shown in FIG. 14. These results indicate that the isocyanuric acid/melamine H-bonding interactions are important in determining the equilibrium constant for aggregation and concomitant changes in absorption.

Figure 16A:
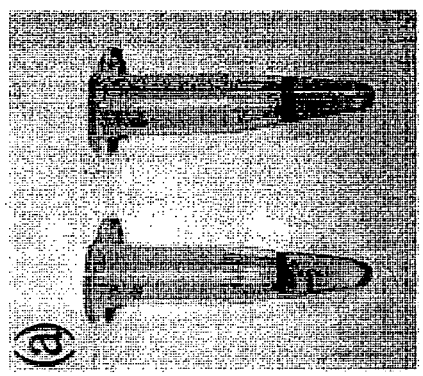
FIG. 16A provides Photograph of 100 μL MH-ICA/NP suspensions in water after addition of 1 μL extracts from unadulterated milk (left) and milk contaminated with 2 ppm melamine (right).
Figure 16B:
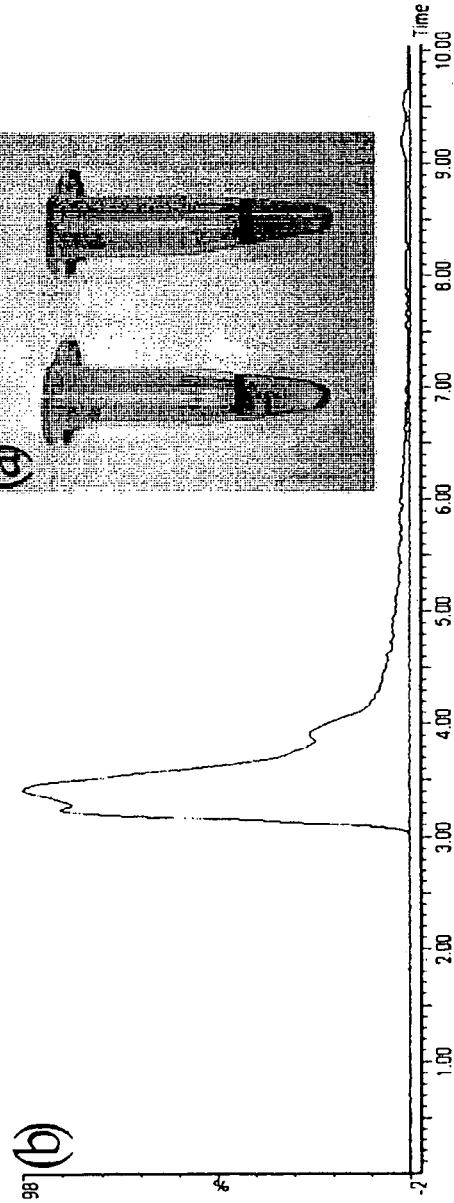
FIG. 16B provides Chromatographs from unadulterated (green) and contaminated (pink) milk. The broad peak centered at 3.5 minutes is due to melamine.

In an illustration of the practical applicability of embodiments of the invention, MH-ICA/NPs were used to examine milk that was intentionally contaminated with 2 ppm melamine. After extracting the milk with 50% aqueous acetonitrile and subsequent washing with dichloromethane, as per FDA protocols, a 1 μL portion of the remaining aqueous solution was added to a 100 μL MH-ICA/NP dispersion in water. As shown in FIG. 16A, the color change is negligible in the case of the original, undoped milk. In contrast, the color turns purple after exposure to the extract from contaminated milk. By comparison to FIG. 14, the solution color indicates that the melamine concentration is between 1 ppm and 10 ppm. To confirm the presence and identity of melamine, the milk extracts were subjected to HPLC/MS as suggested by the FDA (see, e.g. http://www.fsis.usda.gov/PDF/FERN_CHE_0003.pdf). The melamine peak was only detected in the milk containing 2 ppm melamine (FIG. 16B). Mass/e fragmentation patterns characteristic of melamine were also observed, see Supporting Information below.

Supporting Information

For these examples, melamine, cyanuric acid, 1,6-dibromohexane, chloroauric acid, sodium citrate and thiourea were purchased from Aldrich. Regular milk was purchased from a local grocery store. The standard stock solution of melamine in deionized water with concentrations range from 0.01 ppm, 0.1 ppm, 0.2 ppm, 0.5 ppm, 1 ppm, 2 ppm, 5 ppm, 10 ppm, 100 ppm to 1000 ppm were prepared.

¹H and ¹³C NMR spectra to characterize MH-ICA were collected on a Varian Inova 500 MHz NMR spectrometer. HPLC/MS for the detection of extractates from commercial milk fortified with and without melamine was performed in the UC Santa Barbara Mass Spectrometry Lab. UV-Vis absorption spectrum to measure the surface plasmon resonance was conducted on a Shimadzu UV-2401 UV-Vis spectrometer.

A scheme for the synthesis of Mercaptohexyl Isocyanuric Acid (MH-ICA) is shown in FIG. 10A. 6-Bromohexyl isocyanuric acid was synthesized using methods and materials known in the art (see, e.g. Berl et al., Chem. Eur. J. 2000, 6, 1938-1946; and Hoeben et al., Org. Biomol. Chem. 2006, 4, 4460-4462). Briefly, 1-2 Cyanuric acid (6.2 g, 48 mmol) and ground $K_2CO_3$ (1.66 g, 12.0 mmol) were dissolved in DMSO (200 mL). After the mixture was stirred for 30 min, dibromohexane (2.98 g, 12.0 mmol, 0.25 equiv.) was added and was heated to 60° C. for 16 h. Upon cooling down the reaction to room temperature, the mixture solution was partitioned between diethyl ether and saturated $KHSO_4$. The organic fraction was collected and the solvent was removed by rotary evaporator. Recrystallization of the residue from hexane yielded 6-bromohexyl isocyanuric acid which was extensively rinsed with hexane. The product (450 mg) was obtained in high purity. ¹H NMR (500 MHz, DMSO-d6) δ: 11.38 (s, 2H), 3.62 (t, 2H), 3.52 (t, 2H), 1.78 (m, 2H), 1.50 (m, 2H), 1.38 (m, 2H), 1.27 (m, 2H) ppm; ¹³C NMR (125 MHz, DMSO-d6) δ: 149.85, 148.64, 40.28, 35.09, 32.12, 27.21, 27.15, 25.22 ppm. ESI-MS (M+): 293.98 (calculated 293.13).

6-Mercaptohexyl isocyanuric acid (MH-ICA) was synthesized using methods and materials known in the art (see, e.g. Jogireddy et al., J. Synlett 2008, 1219-1221). Briefly, a solution of 6-bromohexyl isocyanuric acid (224 mg, 0.77 mmol) and thiourea (65 mg, 0.853 mmol) in ethanol (40 mL) was degassed (freeze, pump, thaw) thrice, and refluxed under an atmosphere of Ar for 24 h. After cooling down to room temperature, 2 mL NaOH (5 M) aqueous solution was added. The reaction solution was again degassed (freeze, pump, thaw) thrice and slowly heated to reflux. After refluxing for 24 h under Ar atmosphere and cooling down to room temperature, the mixture solution was acidified with 1 mL HCl (2 M) aqueous solution. The precipitate was filtered and extensively washed with deionized $H_2O$ to give the pure product, 6-mercaptohexyl isocyanuric acid (MH-ICA) in a yield of 85% (210 mg). ¹H NMR (500 MHz, DMSO-d6) δ: 11.38 (s, 1H), 3.61 (t, 2H), 2.68 (s, 2H), 1.60 (m, 2H), 1.50 (m, 2H), 1.35 (m, 2H), 1.26 (m, 2H) ppm; ¹³C NMR (125 MHz, DMSO-d6) δ: 149.84, 148.64, 40.32, 37.71, 28.42, 27.41, 27.21, 25.70 ppm. ESI-MS (M+): 246.94 (calculated 246.09).

Preparation of MH-ICA Functionalized Au NPs.

Au NPs (~13 nm, ~10 nM) were synthesized following Frens' method (see, e.g. Frens, G. Nature Phys. Sci. 1973, 241, 20-22). Briefly, MH-ICA was dissolved in pH=9 solution to a concentration of 1 μM. Addition of 5 μL MH-ICA solution to 1 mL Au NPs leads to the formation of MH-ICA/NPs. After centrifugation (10 min, 14,000 g), the supernatant was discarded, and the sediment was redispersed in deionized water to form MH-ICA/NPs dispersion.

Protocol for Extraction and Washing (See Also http://www.fsis.usda.gov/PDF/FERN_CHE_0003.pdf).

Regular milk was extracted with 50% acetonitrile aqueous solution. The extractates were washed with methylene chloride via liquid/liquid phase extraction to remove small organic molecules such as lipids and vitamins.

Melamine Detection

In illustrative embodiments of the invention, a 1 μL standard melamine stock solution, or extractates from regular milk are combined with 100 μL MH-ICA/NPs. After slightly shaking, the solution color was directly visualization and their photograph was taken using a digital camera. The surface plasmon absorption of 200 μL MH-ICA/NPs dispersion before and after addition of 2 μL standard melamine stock solution in 1 mm beam path quartz cell was measured on a Shimadzu UV-2401 UV-Vis spectrometer.

Figure 17:
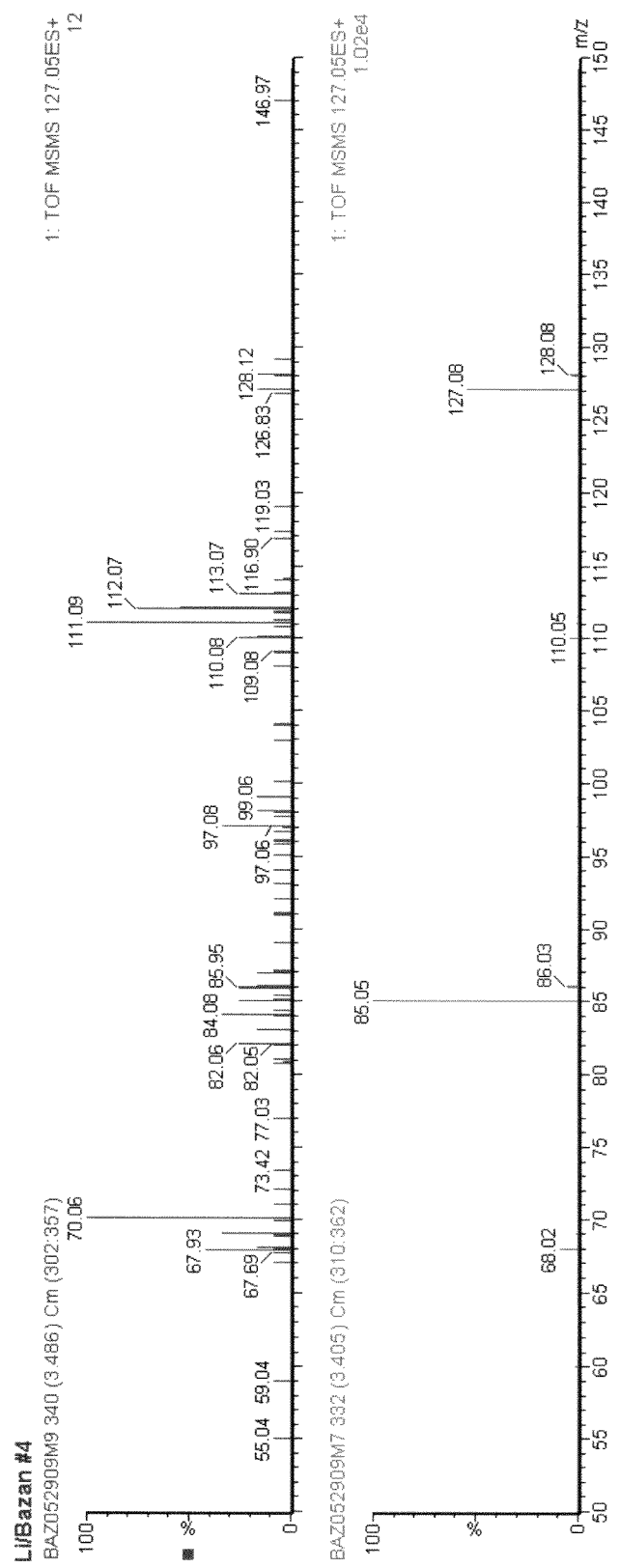
FIG. 17 provides data from ESI-MS of extractates from regular milks with (bottom) and without (top) 2 ppm melamine.

FIG. 17 provides data from ESI-MS of extractates from regular milk with (bottom) and without (top) 2 ppm melamine.

Figure 18A:
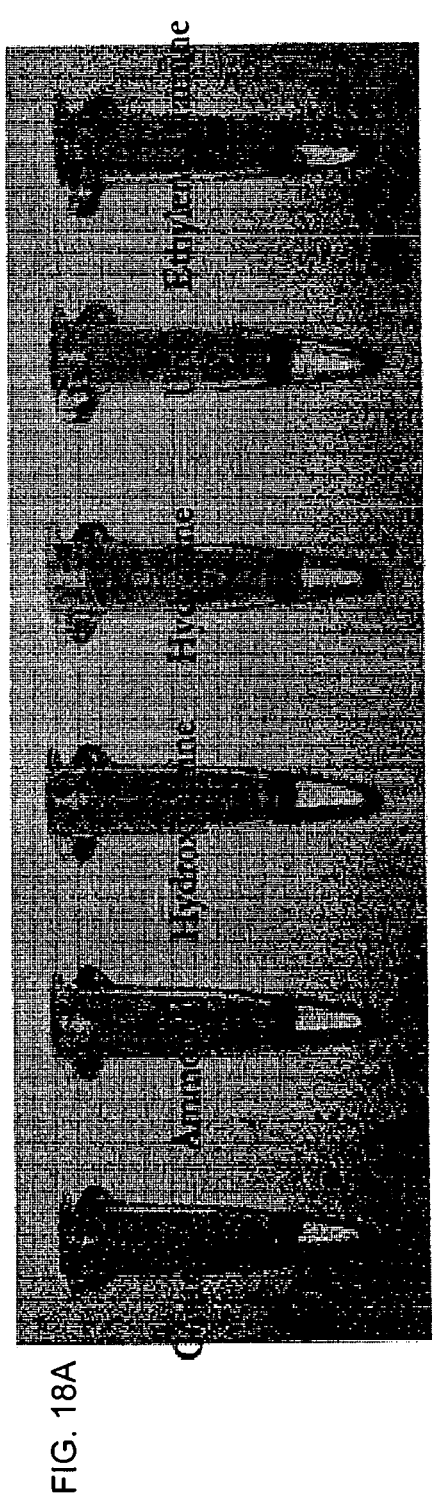
FIG. 18A provides a photograph of 100 μL aqueous dispersion of MH-ICA/NPs upon addition of 1 μL of 1000 ppm ammonia, hydroxylamine, hydrazine, urea and ethylene diamine aqueous solutions (from left to right) respectively.

FIG. 18A provides a photograph of a 100 μL aqueous dispersion of MH-ICA/NPs upon addition of 1 μL of 1000 ppm ammonia, hydroxylamine, hydrazine, urea and ethylene diamine aqueous solutions (from left to right) respectively.

Figure 18B:
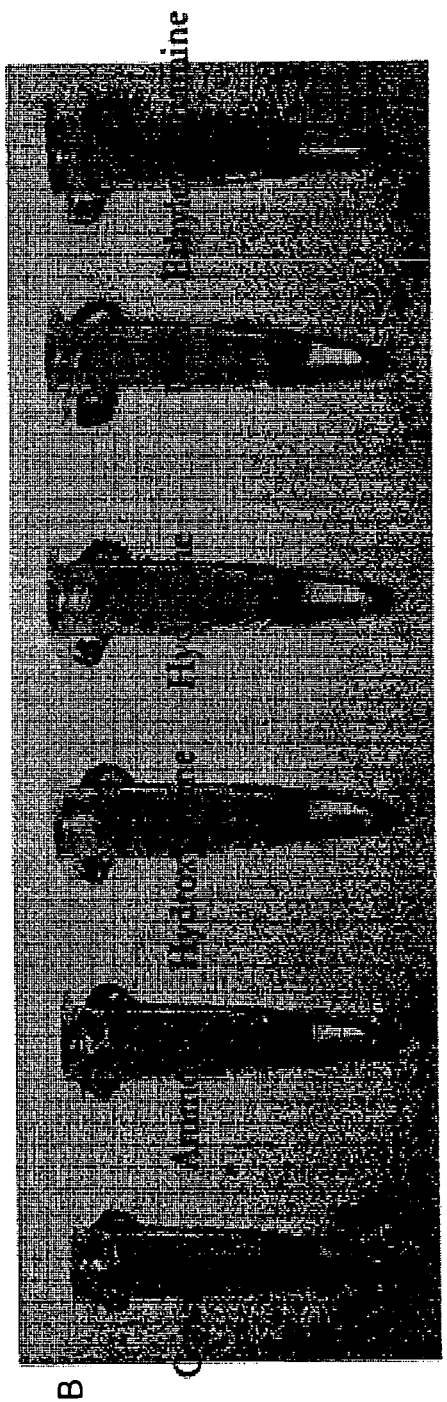
FIG. 18B provides a photograph of 100 μL aqueous dispersion of MH-ICA/NPs upon addition of 1 μL of 2 ppm melamine in the presence of 1000 ppm ammonia, hydroxylamine, hydrazine, urea and ethylene diamine aqueous solutions (from left to right) respectively.

FIG. 18B provides a photograph of a 100 μL aqueous dispersion of MH-ICA/NPs upon addition of 1 μL of 2 ppm melamine in the presence of 1000 ppm ammonia, hydroxylamine, hydrazine, urea and ethylene diamine aqueous solutions (from left to right) respectively.

Figure 15B:
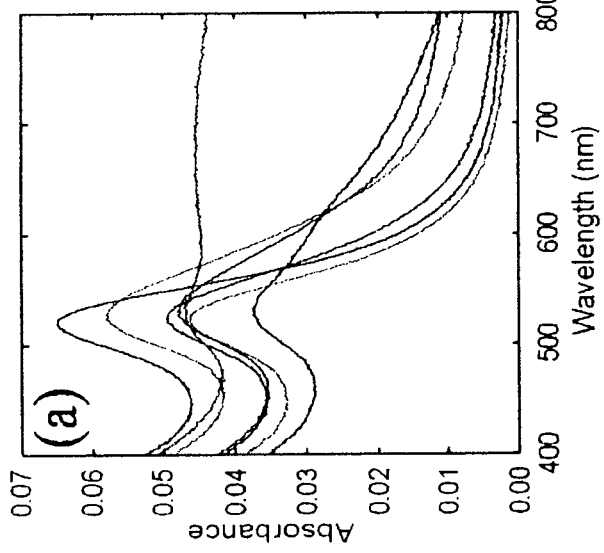
FIG. 15B provides Plot of $A_{620}/A_{520}$ in (a) versus log melamine concentration.

In summary, functionalizing the surface of metallic nanoparticles with isocyanuric acid groups yields responsive plasmonic systems that change color in the presence of melamine. This sensory system is selective, as demonstrated by the absence of response upon addition of various amines. Without being bound by a specific theory or principle, it is believed that the well known multiple H-bonding interactions between melamine and isocyanuric acid induce aggregation and the consequent shifts in the absorption spectra. Simple visual inspection of MH-ICA/NP suspensions can easily distinguish melamine concentrations that fall between 1 to 1000 ppm (e.g. 1 ppm, 10 ppm, 100 ppm, 500 ppm etc.). Lower concentrations can be probed by measuring absorbance spectra and using calibrations curves, as shown in FIGS. 15A and 15B. From a practical perspective, it is noteworthy that the assay described here can be easily incorporated as a final test following well-established protocols for testing contaminated milk. The observation that that no instrumentation is required to observe concentrations of melamine down to 2 ppm (a widely recommended threshold for contamination), demonstrates that one can use embodiments of the invention such as the MH-ICA/NP based assay, and related variations, at milk and other food production sites.

The foregoing written description is considered to be sufficient to enable one skilled in the art to practice the invention. The present invention is not to be limited in scope by the examples presented herein. Indeed, various modifications of the invention in addition to those shown and described herein will become apparent to those skilled in the art from the foregoing description and fall within the scope of the appended claims.

The invention claimed is:

1. A method of detecting melamine in a test sample, comprising:
combining the test sample with a melamine aggregation inducing agent and a plurality of particles in an aqueous media, wherein the particles have an average diameter of between 1 and 2500 nm;
mixing the test sample, the aggregation inducing agent, and the particles to allow melamine in the test sample to interact with the aggregation inducing agent and the particles to produce a change in visual color and a change in turbidity;
monitoring the media to observe the change in visual color and the change in turbidity;

correlating the change in turbidity of the media with the presence of melamine in the test sample; and correlating the change in visual color of the media with a concentration of melamine in the test sample.

2. The method of claim 1, wherein the particles are gold nanoparticles.

3. The method of claim 2, wherein the aggregation inducing agent is cyanuric acid.

4. The method of claim 1, wherein monitoring the change in visual color of the media is performed with a spectrometer.

5. The method of claim 1, wherein the particles produce a change in visual color that is dependent upon the concentration of melamine in the test sample.

* * * * *